(12) United States Patent
Valint, Jr. et al.

(10) Patent No.: US 7,083,646 B2
(45) Date of Patent: *Aug. 1, 2006

(54) SURFACE MODIFICATION OF FUNCTIONAL GROUP-CONTAINING INTRAOCULAR LENSES

(75) Inventors: Paul L. Valint, Jr., Pittsford, NY (US); Joseph A. McGee, Dewitt, NY (US); Wenyan Yan, Fairport, NY (US); Joseph C. Salamone, Boca Raton, FL (US); Daniel M. Ammon, Jr., Rochester, NY (US); Jay F. Kunzler, Canandaigua, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 278 days.

This patent is subject to a terminal disclaimer.

(21) Appl. No.: 10/187,056

(22) Filed: Jun. 28, 2002

(65) Prior Publication Data

US 2004/0006386 A1    Jan. 8, 2004

(51) Int. Cl.
*A61F 2/16* (2006.01)
(52) U.S. Cl. .................. 623/6.62; 623/4.1; 623/6.56
(58) Field of Classification Search ................ 623/4.1, 623/6.11, 6.16, 6.17, 6.56, 6.62
See application file for complete search history.

(56) References Cited

U.S. PATENT DOCUMENTS

| | | | | |
|---|---|---|---|---|
| 5,326,506 A | * | 7/1994 | Vanderbilt | 264/1.7 |
| 5,652,014 A | * | 7/1997 | Galin et al. | 427/2.24 |
| 6,099,852 A | * | 8/2000 | Jen | 424/429 |
| 6,180,687 B1 | * | 1/2001 | Hammer et al. | 522/156 |
| 6,190,410 B1 | * | 2/2001 | Lamielle et al. | 623/6.51 |
| 6,406,739 B1 | | 6/2002 | LeBoeuf et al. | 427/2.24 |
| 6,428,839 B1 | * | 8/2002 | Kunzler et al. | 427/2.1 |
| 6,440,571 B1 | * | 8/2002 | Valint et al. | 428/447 |
| 6,599,559 B1 | * | 7/2003 | McGee et al. | 427/2.24 |
| 6,638,563 B1 | * | 10/2003 | McGee et al. | 427/2.24 |

FOREIGN PATENT DOCUMENTS

WO    WO 97/21497    6/1997

OTHER PUBLICATIONS

Polymeric Materials Science and Engineering, Washington DC vol. 76, Apr. 13, 1997 Surface-Active Macromonomers for Coating of Contact Lens Polymers 2 pages.

* cited by examiner

*Primary Examiner*—Corrie McDermott
*Assistant Examiner*—William H Matthews
(74) *Attorney, Agent, or Firm*—Toan P. Vo

(57) ABSTRACT

Surface modified medical devices such as intraocular lens implants formed from one or more functional group-containing materials using reactive, hydrophilic polymers for the purpose of reducing or eliminating lens epithelial cell growth thereon, reducing or eliminating silicone oil absorption upon subsequent surgical exposure and/or reducing or eliminating implantation inserter friction is provided herein. Additionally, a method of making and using surface modified intraocular lens implants is provided.

24 Claims, 9 Drawing Sheets

SURFACE MODIFICATION OF FUNCTIONAL GROUP-CONTAINING INTRAOCULAR LENSES

FIELD OF THE INVENTION

The present invention relates generally to surface modification of functional group-containing polymeric materials used in the manufacture of medical device implants. More specifically, the present invention relates to surface modification of intraocular lens implants formed from one or more functional group-containing materials using reactive, hydrophilic polymers for the purpose of reducing or eliminating lens epithelial cell growth thereon.

BACKGROUND OF THE INVENTION

Since the 1940's ophthalmic devices in the form of intraocular lens (IOL) implants have been utilized as replacements for diseased or damaged natural ocular lenses. In most cases, an IOL is implanted within an eye at the time of surgically removing the diseased or damaged natural lens, such as for example, in the case of cataracts. For decades, the preferred material for fabricating such IOL implants was poly(methyl methacrylate) (PMMA), which is a rigid, glassy polymer.

Softer, more flexible IOL implants have gained in popularity in more recent years due to their ability to be compressed, folded, rolled or otherwise deformed. Such softer IOL implants may be deformed prior to insertion thereof through an incision in the cornea of an eye. Following insertion of the IOL in an eye, the IOL returns to its original pre-deformed shape due to the memory characteristics of the soft material. Softer, more flexible IOL implants as just described may be implanted into an eye through an incision that is much smaller, i.e., less than 4.0 mm, than that necessary for more rigid IOLs, i.e., 5.5 to 7.0 mm. A larger incision is necessary for more rigid IOL implants because the lens must be inserted through an incision in the cornea slightly larger than the diameter of the inflexible IOL optic portion. Accordingly, more rigid IOL implants have become less popular in the market since larger incisions have been found to be associated with an increased incidence of postoperative complications, such as induced astigmatism.

With recent advances in small-incision cataract surgery, increased emphasis has been placed on developing soft, foldable materials suitable for use in the manufacture of IOL implants. In general, the materials of current commercial IOLs fall into one of three categories: silicone, hydrophilic acrylic and hydrophobic acrylic.

In general, IOLs, once implanted, have a tendency to allow lens epithelial cells (LECs) to attach and spread on the surface of the IOL. Such LEC growth on IOL surfaces causes undesirable IOL opacification requiring IOL explantation and replacement. Also undesirable, IOLs manufactured from silicone materials tend to absorb silicone oils used in subsequent unrelated ocular surgeries causing opacification of the IOL.

Because of the noted shortcomings of current biocompatible polymeric materials available for use in the manufacture of ophthalmic devices such as IOLs, there is a need for stable, biocompatible polymeric materials suitable for use in the manufacture of IOLs that reduce or eliminate LEC growth on surfaces thereof upon implantation-and reduce or eliminate the risk of IOL absorption of silicone oil in the case of subsequent ocular surgeries.

SUMMARY OF THE INVENTION

Surface modification of functional group-containing polymeric materials useful in the manufacture of medical device implants such as intraocular lenses (IOLs) in accordance with the present invention utilizes reactive, hydrophilic polymers. Reactive, hydrophilic polymers are used to form covalent chemical linkages with the surface of IOLs or like implants manufactured from functional group-containing polymeric materials. The preferred reactive, hydrophilic polymers of the present invention are selected based on the specific functional group-containing polymeric material to be coated. In accordance with the present invention, the one or more reactive, hydrophilic polymers selected for surface modification must have complementary chemical functionality to that of the one or more functional group-containing polymeric materials. Such complementary chemical functionality enables a chemical reaction between the functional groups of the polymeric material and the reactive, hydrophilic polymer to form covalent chemical linkages therebetween. The one or more reactive, hydrophilic polymers are thus chemically bound to the surface of the one or more functional group-containing polymeric materials of the IOL or like medical device implant to achieve surface modification thereof. Such surface modification of an IOL implant reduces or eliminates silicone oil absorption upon subsequent exposure, reduces or eliminates surface calcification, reduces or eliminates lens epithelial cell surface growth and/or reduces friction upon passage through an inserter for implantation.

Accordingly, it is an object of the present invention to provide a surface modifying coating for biocompatible polymeric compositions having desirable physical characteristics for use in the manufacture of ophthalmic devices.

Another object of the present invention is to provide a surface modifying coating for polymeric compositions having a relatively high refractive index.

Another object of the present invention is to provide a surface modifying coating for polymeric compositions suitable for use in the manufacture of an ophthalmic implant.

Another object of the present invention is to provide a surface modifying coating for polymeric compositions that reduces or eliminates lens epithelial cell growth and/or posterior capsular opacification following implantation thereof in an eye.

Another object of the present invention is to provide a surface modifying coating for polymeric compositions that reduces or eliminates surface calcification following implantation thereof in an eye.

Another object of the present invention is to provide a surface modifying coating for surgical implants that reduces friction of the coated implant when passed through an implantation inserter.

Still another object of the present invention is to provide a surface modifying coating for polymeric compositions that is relatively simple to produce and use.

These and other objectives and advantages of the present invention, some of which are specifically described and others that are not, will become apparent from the detailed description and claims that follow.

DETAILED DESCRIPTION OF THE INVENTION

Figure 1:
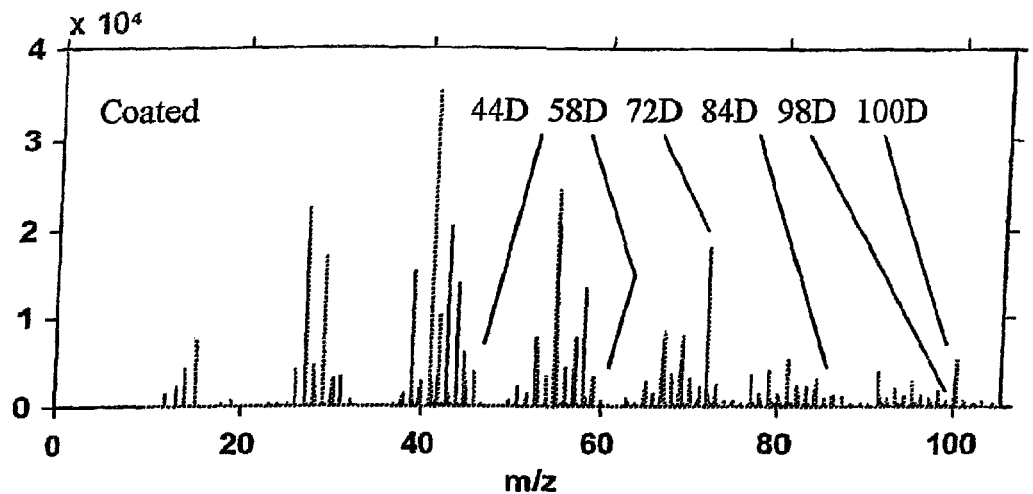
FIG. 1 shows the ToF-SIMS spectrum of poly(DMA-co-GMA) coated lens implants of sample set one.

Surface structure and composition determine many of the physical properties and ultimate uses of solid materials. Characteristics such as wetting, friction, electrostatic charging and adhesion are largely influenced by surface characteristics. Of particular concern are the effects of such surface characteristics on biocompatibility. The alteration of surface characteristics is therefore of special significance in biotechnical applications such as in the case of medical device implants.

The following detailed description is provided to enable any person skilled in the art to which the present invention pertains to make and use the same, and sets forth the best mode contemplated by the inventors of carrying out the subject invention.

The present invention is a method of surface modifying intraocular lenses (IOLs) and like medical devices or implants through the use of complementary reactive functionality. Although only IOLs will be referred to hereinafter for purposes of simplicity, such reference is not intended to be limiting since the subject method is suitable for surface modification of other medical devices and implants, as well as IOLs. For surface modification of IOLs in accordance with the present invention, complementary reactive functionality is incorporated between the IOL material and the surface modification treatment polymer (SMTP). For example, if a reactive hydrophilic SMTP has epoxide functionality, then the IOL material to be treated must have a complementary functionality that will react with that of the SMTP. In such a case, the IOL material could include an alcohol-based monomer such as 2-hydroxyethyl methacrylate to react with the SMTP epoxide functionality. Likewise, if an IOL is formed from an epoxide monomer-containing material, a hydrophilic SMTP containing a 2-hydroxyethyl methacrylate copolymer could be used for surface modification in accordance with the present invention.

More specifically, surface modification of IOLs in accordance with the present invention requires one or more reactive, hydrophilic SMTPs. The reactive, hydrophilic SMTPs of the present invention are copolymers of various hydrophilic monomers with a monomer having reactive chemical functionality. The hydrophilic monomers can be aprotic types such as acrylamides and N-vinylpyrrolidone or protic types such as methacrylic acid and 2-hydroxyethyl methacrylate. Examples of suitable hydrophilic monomers include but are not limited to N,N-dimethylacrylamide, N,N-dimethylmethacrylamide, N-methylmethacrylamide and N-methylacrylamide but preferably N,N-dimethylacrylamide for increased hydrophilicity. Suitable monomers having reactive chemical functionality include for example but are not limited to monomers having epoxide, carboxylic acid, anhydride, oxazolone and alcohol functionalities. Examples of suitable reactive, hydrophilic SMTPs include but are not limited to copolymers and terpolymers of the monomers having reactive chemical functionality described above. Such reactive, hydrophilic SMTPs are produced through free radical polymerization techniques known to those skilled in the art.

Suitable functional group-containing polymeric materials useful in the manufacture of IOLs or like medical device implants in accordance with the present invention have clarity, a relatively high refractive index of approximately 1.40 or greater, a relatively low glass transition temperature of approximately 250 Celsius or less, and a relatively high elongation of approximately 80 percent or greater. Such functional group-containing polymeric materials of the present invention, possessing the particular physical characteristics described, likewise possess functional groups such as for example but not limited to hydroxy functional groups, carboxylic acid functional groups, oxazolone functional groups, anhydride functional groups and epoxide functional groups. Examples of suitable polymeric materials having hydroxy functional groups include but are not limited to 2-hydroxyethyl methacrylate, glyceryl methacrylate and 3-hydroxypropyl methacrylamide. Examples of suitable polymeric materials having carboxylic acid functional groups include but are not limited to methacrylic acid, acrylic acid and N-carboxy-β-alanine-N-vinyl ester. Examples of suitable polymeric materials having oxazolinone functional groups include but are not limited to 2-isopropenyl-4,4-dimethyl-2-oxazolin-5-one, 2-vinyl-4,4-dimethyl-2-oxazolin-5-one, spiro-4'-(2'-isopropenyl-2'-oxazolin-5-one)cyclohexane, spiro-4'-(2'-vinyl-2'-oxazolin-5'-one)cyclohexane and 2-(1-propenyl)-4,4-dimethyl-oxazolin-5-one. Examples of suitable polymeric materials having anhydride functional groups include but are not limited to methacrylic anhydride, maleic anhydride and acrylic anhydride. An example of a suitable polymeric material having epoxide functional groups includes but is not limited to glycidyl methacrylate.

Suitable functional group-containing polymeric materials for the production of IOLs in accordance with the present invention include but are not limited to foldable or compressible materials, such as silicone polymers, hydrocarbon and fluorocarbon polymers, hydrogels, soft acrylic polymers, polyesters, polyamides, polyurethane, silicone polymers with hydrophilic monomer units, fluorine-containing polysiloxane elastomers and combinations thereof. One preferred functional group-containing polymeric material of the present invention is a hydrogel made from 2-hydroxyethyl methacrylate (HEMA) and 6-hydroxyhexyl methacrylate (HOHEXMA), i.e., poly(HEMA-co-HOHEXMA). Poly(HEMA-co-HOHEXMA) is a preferred polymeric material for the manufacture of IOL implants due to its equilibrium water content of approximately 18 percent by weight, and high refractive index of approximately 1.474, which is greater than that of the aqueous humor of the eye, i.e., 1.336. A high refractive index is a desirable feature in the production of IOLs to impart high optical power with a minimum of optic thickness. By using a material with a high refractive index, visual acuity deficiencies may be corrected using a thinner IOL. Poly(HEMA-co-HOHEXMA) is a desirable material in the production of IOL implants due to its mechanical strength, which is suitable to withstand considerable physical manipulation. Poly(HEMA-co-HOHEXMA) also has desirable recovery properties suitable for IOL implant use. IOL implants manufactured from a material possessing desirable recovery properties such as poly (HEMA-co-HOHEXMA) unfold in a more controlled manner in an eye, rather than explosively, to its predetermined shape. Explosive unfolding of IOL implants is undesirable due to potential damage to delicate tissues within the eye. Poly(HEMA-co-HOHEXMA) also has dimensional stability in the eye, which is likewise desirable.

Although the teachings of the present invention are preferably applied to soft or foldable IOL implants or like medical device implants formed of a foldable or compressible material, the same may also be applied to harder, less flexible lenses formed of a relatively rigid material such as poly(methyl methacrylate) (PMMA) having flexible haptics formed either of the same or a different material.

In accordance with the present invention, the one or more functional group-containing polymeric materials are used to produce an IOL implant containing functional groups. One or more reactive, hydrophilic SMTPs of the present invention as described-above, are then selected so as to have chemical functionality complementary to that of the one or more functional group-containing polymeric materials comprising the IOL. Such complementary chemical functionality enables a chemical reaction to occur between the functional groups at the surface of the polymeric material forming the IOL and the functional groups of the one or more reactive, hydrophilic SMTPs. This chemical reaction between functional groups forms covalent chemical linkages therebetween. For example, an IOL polymeric material having hydroxy functional groups would preferably undergo surface modification using reactive, hydrophilic SMTPs containing carboxylic acid functional groups, isocyanate functional groups or epoxy functional groups. Likewise, an IOL polymeric material having carboxylic acid groups would preferably undergo surface modification using reactive, hydrophilic SMTPs containing glycidyl methacrylate (GMA) monomer units to provide epoxy functional groups.

Surface modification of IOLs produced from one or more functional group-containing polymeric materials using one or more reactive, hydrophilic SMTPs in accordance with the present invention is described in still greater detail in the examples that follow.

EXAMPLE 1

Synthesis of Reactive, Hydrophilic Copolymer of N,N-dimethylacrylamide (DMA) and Glycidyl Methacrylate (GMA)

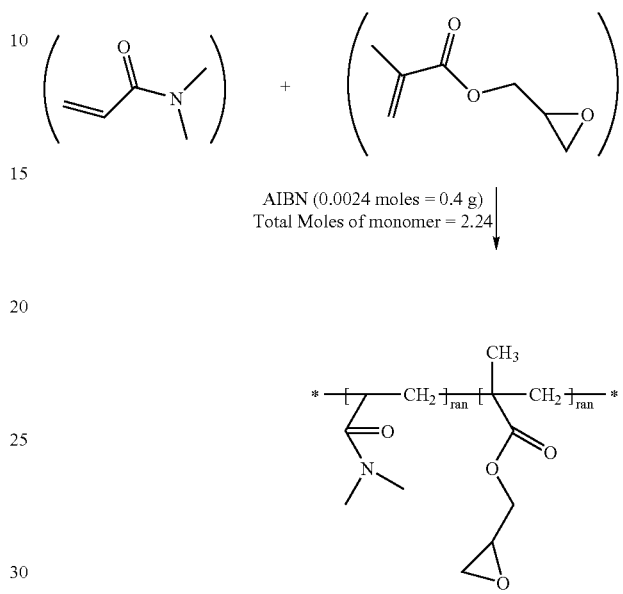

DMA-co-GMA [x=86, y=14] To a 3 liter (L) reaction flask were added distilled N,N-dimethylacrylamide (DMA, 192 g, 1.92 moles), distilled glycidyl methacrylate (GMA, 48 g, 0.32 moles) 2,2'-azobisisobutyronitrile (AIBN, 0.4 g, 0.0024 moles) and tetrahydrofurarn (2000 ml). The reaction vessel was fitted with a mechanical stirrer, condenser, thermal controller and a nitrogen inlet. Nitrogen was bubbled through the solution for 15 minutes to remove any dissolved oxygen. The reaction flask was then heated to 60° C. under a passive blanket of nitrogen for 24 hours. The reaction mixture was then added slowly to 12 L of ethyl ether with good mechanical stirring. The reactive polymer precipitated and was collected by vacuum filtration. The solid was placed in a vacuum oven at 30° C. overnight to remove the ether leaving 213.85 g of reactive polymer (89% yield). The reactive polymer was placed in a desiccator for storage until use.

The general procedure of Example 1 was followed to prepare the SMTPs (Examples 2–5) listed in Table 1 below.

TABLE 1

Examples 2–5: Reactive DMA-co-GMA Polymers

| Example | DMA grams | DMA moles | DMA x mole % | GMA grams | GMA moles | GMA y mole % | AIBN mo/es | Solvent | volume ml | Time (hours) |
|---|---|---|---|---|---|---|---|---|---|---|
| 2 | 57 | 0.58 | 97 | 3 | 0.02 | 3 | 0.0006 | toluene | 600 | 20 |
| 3 | 54 | 0.54 | 93 | 6 | 0.042 | 7 | 0.0006 | toluene | 600 | 20 |
| 4 | 42 | 0.42 | 76 | 18 | 0.13 | 24 | 0.0006 | toluene | 600 | 20 |
| 5 | 36 | 0.36 | 68 | 24 | 0.17 | 32 | 0.0006 | toluene | 600 | 20 |

EXAMPLE 6

Synthesis of Reactive, Hydrophilic Copolymer of N,N-dimethylacrylamide (DMA), 1H,1H,5H-octafluoropentyl Methacrylate (OFPMA) and Glycidyl Methacrylate (GMA)

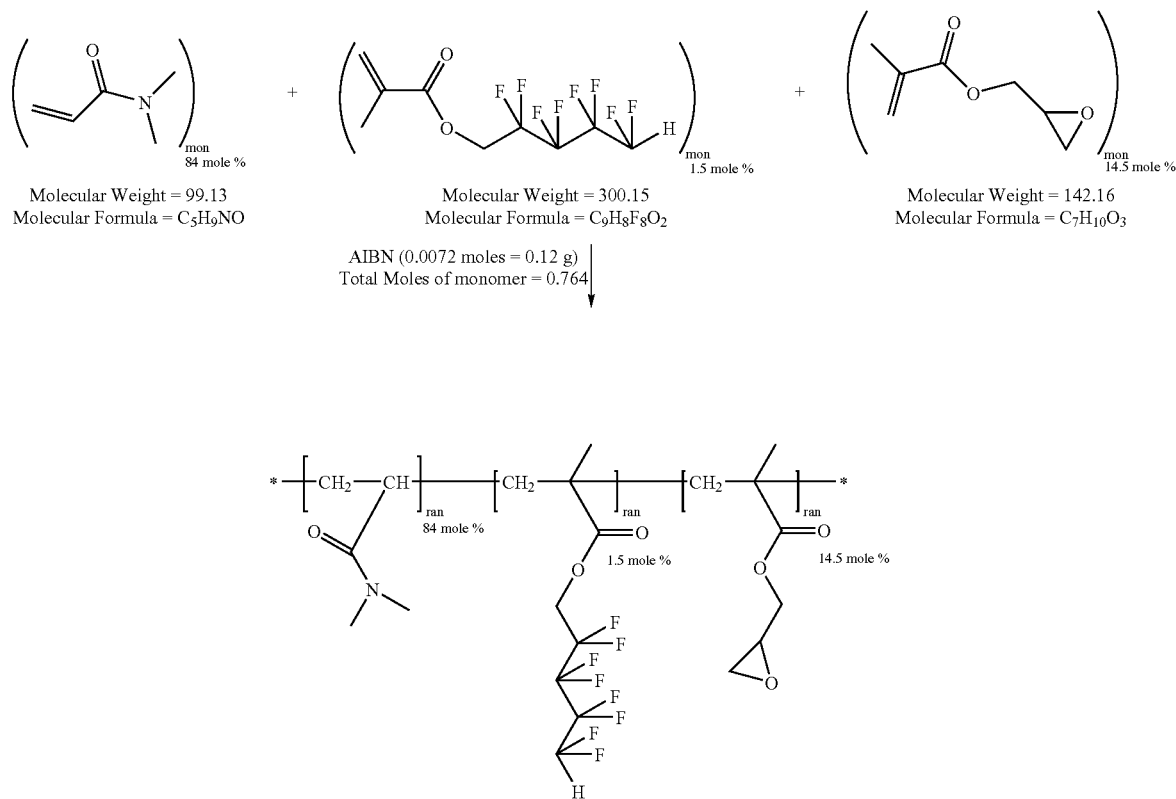

To a 1000 ml reaction flask were added distilled N,N-dimethylacrylamide (DMA, 64 g, 0.64 moles), 1H,1H,5H-octafluoropentyl methacrylate (OFPMA, 4 g, 0.012 moles, used as received), distilled glycidyl methacrylate (GM, 16 g, 0.112 moles) 2,2'-azobisisobutyronitrile (AIBN, 0.12 g, 0.00072 moles) and tetrahydrofuran (1200 ml). The reaction vessel was fitted with a magnetic stirrer, condenser, thermal controller and a nitrogen inlet. Nitrogen was bubbled through the solution for 15 minutes to remove any dissolved oxygen. The reaction flask was then heated to 60° C. under a passive blanket of nitrogen for 20 hours. The reaction mixture was then added slowly to 6 L of ethyl ether with good mechanical stirring. The reactive polymer precipitated and was collected by vacuum filtration. The solid was placed in a vacuum oven at 30° C. overnight to remove the ether leaving 66.1 g of reactive polymer (79% yield). The reactive polymer was placed in a desiccator for storage until use.

The general procedure of Example 6 above was followed to prepare the SMTPs (Examples 7–10) listed in Table 2 below. Reaction times for the synthesis of each SMTP of Table 2 below were 20 hours and the solvent was tetrahydrofuran (600 ml). The AIBN levels for each SMTP of Table 2 were 0.0006 moles.

TABLE 2

Examples 7–10: Reactive DMA-co-OFPMA-co-GMA Polymers

| Example | DMA grams | DMA moles | DMA x mole % | OFPMA grams | OFPMA moles | OFPMA y mole % | GMA grams | GMA moles | GMA z mole % | Yield grams % |
|---|---|---|---|---|---|---|---|---|---|---|
| 7 | 51.4 | 0.52 | 91 | 2.6 | 0.0087 | 1.5 | 6 | 0.042 | 7.4 | 47.6 |
| 8 | 39.5 | 0.4 | 74.3 | 2.5 | 0.0083 | 1.5 | 18 | 0.13 | 24.2 | 50.2 |
| 9 | 33.6 | 0.34 | 65.7 | 2.4 | 0.008 | 1.5 | 24 | 0.17 | 32.8 | 48.8 |
| 10 | 54.4 | 0.55 | 95 | 2.65 | 0.0088 | 1.5 | 3 | 0.02 | 3.5 | 40.2 |

In accordance with the present invention, methoxypolyoxyethylene methacrylate would be a third monomer giving rise to a SMTP with grafted polyoxyethylene sidechains and epoxy groups as the reactive chemical functionality.

EXAMPLE 11

Synthesis of Reactive, Hydrophilic Copolymer of N,N-dimethylacrylamide (DMA), 1H,1H,5H-octafluoropentyl Methacrylate (OFPMA), Glycidyl Methacrylate (GMA) and Polyethylene Glycol 1000 Monomethylether Methacrylate (PEGMA)

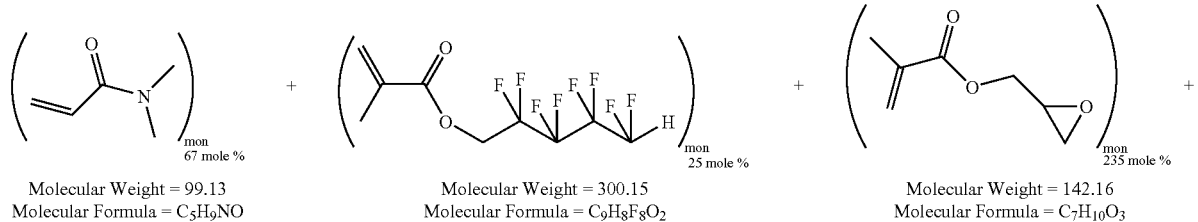

Molecular Weight = 99.13
Molecular Formula = $C_5H_9NO$

Molecular Weight = 300.15
Molecular Formula = $C_9H_8F_8O_2$

Molecular Weight = 142.16
Molecular Formula = $C_7H_{10}O_3$

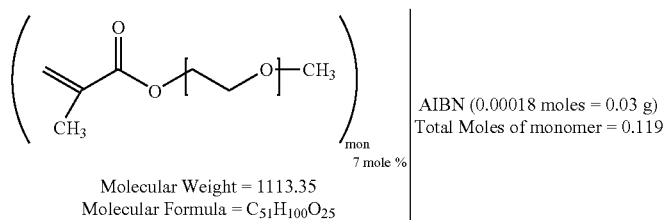

Molecular Weight = 1113.35
Molecular Formula = $C_{51}H_{100}O_{25}$

AIBN (0.00018 moles = 0.03 g)
Total Moles of monomer = 0.119

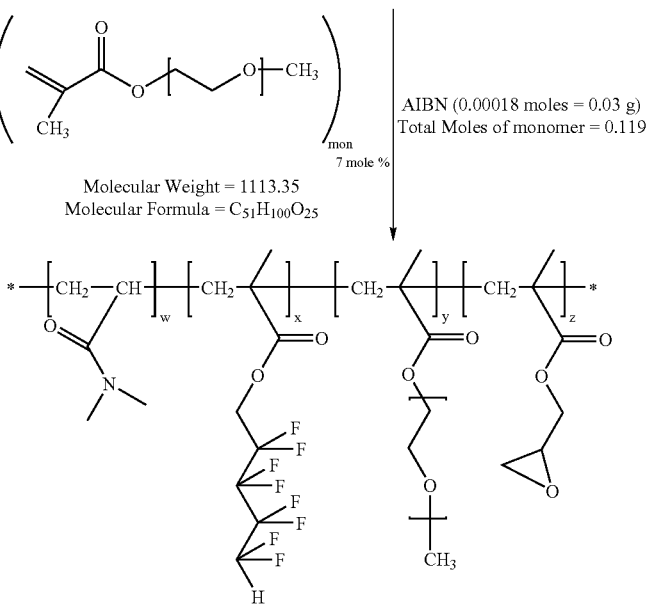

To a 500 ml reaction flask were added distilled N,N-dimethylacrylamide (DMA, 8 g, 0.08 moles), 1H,1H,5H-octafluoropentyl methacrylate (OFPMA, 1 g, 0.003 moles, used as received), distilled glycidyl methacrylate (GM, 4 g, 0.028 moles) Polyethylene glycol 1000 monomethyl ether methacrylate (PEGMA, 8 g, 0.007 moles), 2,2'-azobisisobutyronitrile (AIBN, 0.03 g, 0.00018 moles) and tetrahydrofuran (300 ml). The reaction vessel was fitted with a magnetic stirrer, condenser, thermal controller and a nitrogen inlet. Nitrogen was bubbled through the solution for 15 minutes to remove any dissolved oxygen. The reaction flask was then heated to 60° C. under a passive blanket of nitrogen for 72 hours. Flash evaporation of the solvent followed by freeze drying left 8.8 g of reactive polymer (42% yield), a wax like semi-solid.

EXAMPLE 12

Synthesis of Reactive, Hydrophilic Copolymer of N-Vinyl-2-pyrrolidinone (NVP) and 4-Vinvicyclohexyl-1,2-epoxide (VCHE)

Molecular Weight = 111.14
Molecular Formula = $C_6H_9NO$

+

-continued

Molecular Weight = 124.18
Molecular Formula = $C_8H_{12}O$

AIBN (.05 g, .0003 moles)
600 ml THF

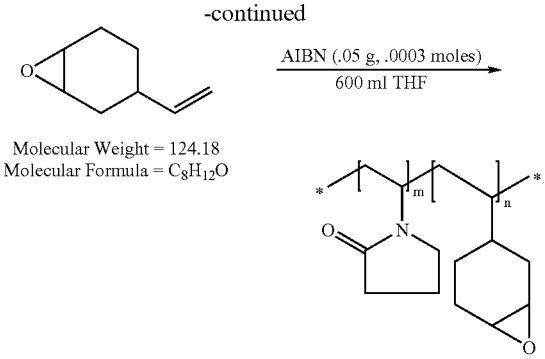

To a 1 L reaction flask were added distilled N-vinyl-2-pyrrolidinone (NVP, 53.79 g, 0.48 moles), 4-vinylcyclohexyl-1,2-epoxide (VCHE, 10.43 g, 0.084 moles), 2,2'-azobisisobutyronitrile (AIBN, 0.05 g, 0.0003 moles) and THF (600 ml). The reaction vessel was fitted with a magnetic stirrer, condenser, thermal controller and a nitrogen inlet. Nitrogen was bubbled through the solution for 15 minutes to remove any dissolved oxygen. The reaction flask was then heated to 60° C. under a passive blanket of nitrogen for 20 hours. The reaction mixture was then added slowly to 6 L of ethyl ether with good mechanical stirring. The copolymer precipitated and was collected by vacuum filtration. The solid was placed in a vacuum oven at 30° C. overnight to remove the ether leaving 21 g of reactive polymer (a 32% yield). The reactive polymer was placed in a desiccator for storage until use.

EXAMPLE 13

Synthesis of A Reactive Hydrophilic Copolymer of N,N-dimethylacrylamide (DMA), Lauryl Methacrylate (LMA) and Glycidyl Methacrylate (GMA)

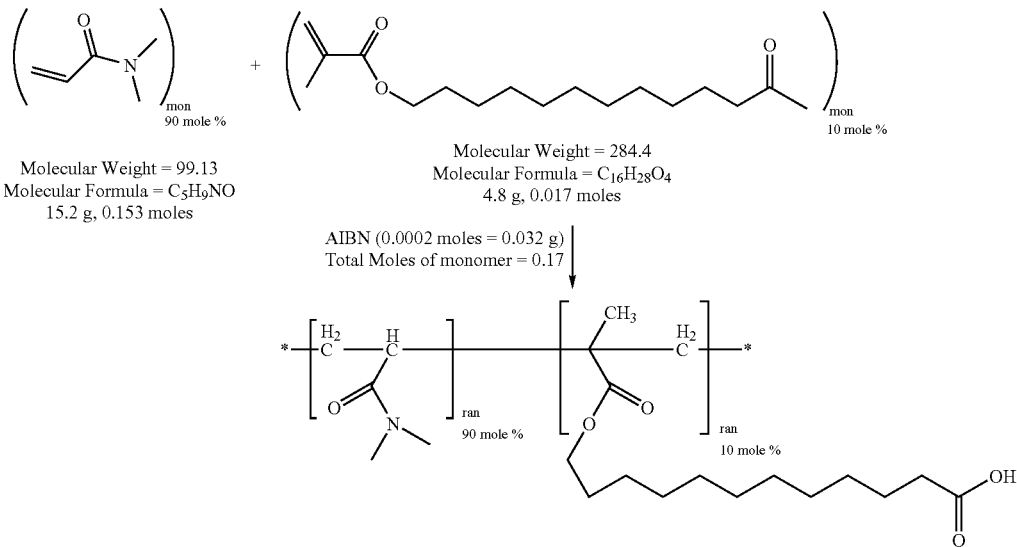

To a 1000 ml reaction flask were added distilled N,N-dimethylacrylamide (DMA, 32 g, 0.32 moles), lauryl methacrylate (LMA, 1.5 g, 0.006 moles, used as received), distilled glycidyl methacrylate (GM, 8 g, 0.056 moles) 2,2'-azobisisobutyronitrile (AIBN, 0.06 g, 0.00036 moles) and tetrahydrofuran (600 ml). The reaction vessel was fitted with a magnetic stirrer, condenser, thermal controller and a nitrogen inlet. Nitrogen was bubbled through the solution for 15 minutes to remove any dissolved oxygen. The reaction flask was then heated to 60° C. under a passive blanket of nitrogen for 20 hours. The reaction mixture was then added slowly to 3 L of ethyl ether with good mechanical stirring. The reactive polymer precipitated and was collected by vacuum filtration. The solid was placed in a vacuum oven at 30° C. overnight to remove the ether leaving 29.2 g of reactive polymer (70% yield). The reactive polymer was placed in a desiccator for storage until use.

EXAMPLE 14

Synthesis of Reactive, Hydrophilic Copolymer of N,N-dimethylacrylamide (DMA) and Methacrylic Acid (MAA)

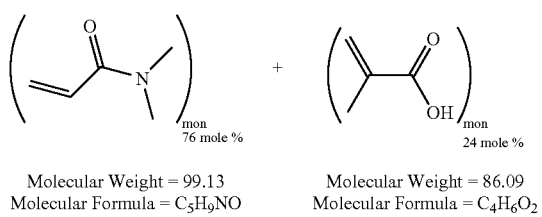

-continued

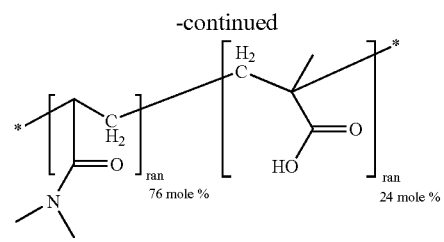

To a 3000 ml reaction flask were added distilled N,N-dimethylacrylamide (DMA, 128 g, 1.28 moles), methacrylic acid (MAA, 32 g, 0.37 moles) 2,2'-azobisisobutyronitrile (AIBN, 0.24 g, 0.0016 moles) and anhydrous 2-propanol (2000 ml). The reaction vessel was fitted with a magnetic stirrer, condenser, thermal controller and a nitrogen inlet.

Nitrogen was bubbled through the solution for 15 minutes to remove any dissolved oxygen. The reaction flask was then heated to 60° C. under a passive blanket of nitrogen for 72 hours. The volume of the reaction mixture was reduced to half by flash evaporation. The reactive polymer was precipitated into 8L of ethyl ether and then collected by vacuum filtration. The solid was placed in a vacuum oven at 30° C. overnight to remove the ether leaving 142.34 g of reactive polymer (89% yield). The reactive polymer was placed in a desiccator for storage until use.

The general procedure of Example 14 was followed to prepare the SMTP (Examples 15–16) listed in Table 3 below.

To a 500 ml reaction flask were added distilled N,N-dimethylacrylamide (DMA, 15.2 g, 0.153 moles), 12-methacryloyloxydodecanoic acid (LMAA, 4.8 g, 0.017 moles) 2,2'-azobisisobutyronitrile (AIBN, 0.032 g, 0.0002 moles) and anhydrous tetrahydrofuran (200 ml). The reaction vessel was fitted with a magnetic stirrer, condenser, thermal controller and a nitrogen inlet. Nitrogen was bubbled through the solution for 15 minutes to remove any dissolved oxygen. The reaction flask was then heated to 60° C. under a passive blanket of nitrogen for 72 hours. The reaction mixture was then added slowly to 2.5L of heptane with good mechanical stirring. The reactive polymer precipitated and was collected

TABLE 3

Examples 15–16: Reactive polymers DMA-co-MAA

| Example | DMA grams | DMA moles | DMA x mole % | MAA grams | MAA moles | MAA y mole % | AIBN moles | Solvent | volumn ml | Time (hours) | Yield grams % |
|---|---|---|---|---|---|---|---|---|---|---|---|
| 15 | 42 | 0.42 | 67 | 18 | 0.21 | 33 | 0.0006 | 2-propanol | 750 | 72 | 49.63 |
| 16 | 36 | 0.36 | 56 | 24 | 0.28 | 44 | 0.0006 | 2-propanol | 750 | 72 | 44.97 |

In accordance with the present invention, methoxypolyoxyethylene methacrylate would be a third monomer giving rise to a coating polymer with grafted polyoxyethylene sidechains and carboxylic acid groups as the reactive chemical functionality.

EXAMPLE 17

Synthesis of a Hydrophilic Reactive Polymer of N,N-dimethylacrylamide (DMA) and 12-Methacrylovioxydodecanoic Acid (LMAA)

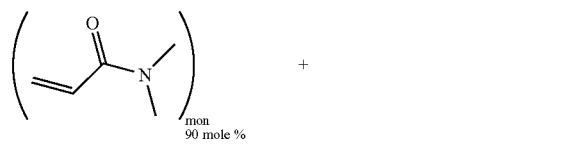

90 mole %
Molecular Weight = 99.13
Molecular Formula = $C_5H_9NO$
15.2 g, 0.153 moles

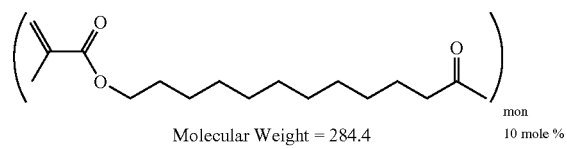

10 mole %
Molecular Weight = 284.4
Molecular Formula = $C_{16}H_{28}O_4$
4.8 g, 0.017 moles AIBN (0.0002 moles = 0.032 g)
Total Moles of monomer = 0.17 | THF

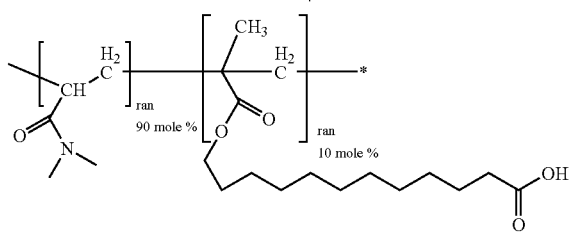

by vacuum filtration. The solid was placed in a vacuum oven at 30° C. overnight to remove the ether leaving 15 g of reactive polymer (75% yield). The reactive polymer was placed in a desiccator for storage until use.

EXAMPLE 18

Surface Modification of Poly(HEMA-co-HOHEXMA) Intraocular Lens Implant with Reactive, Hydrophilic Copolymer of N,N-dimethylacrylamide (DMA) and Glycidyl Methacrylate (GMA) from Example 1

Poly(HEMA-co-HOHEXMA) intraocular lens implants were surface modified or coated by placing the intraocular lens implants in a container and adding a 1.0 percent by weight poly(DMA-co-GMA [86/14 mole %]) solution to the container to cover the intraocular lens implants. The container containing the intraocular lens implants covered in solution was then autoclaved for 59 minutes at 121°Celsius. The container was then removed from the autoclave and the intraocular lens implants were removed from the solution. The intraocular lens implants were then rinsed three times in a buffered saline solution.

EXAMPLE 19

Surface Analysis of Poly(HEMA-co-HOHEXMA) Intraocular Lens Implant Surface Modified with Reactive, Hydrophilic Copolymer of N,N-dimethylacrylamide (DMA) and Glycidyl Methacrylate (GMA)

Surface analysis was conducted on three separate sample sets. The first sample set (Sample Set One or SSO) included control and poly(DMA-co-GMA) coated poly(HEMA-co-HOHEXMA) intraocular lens implants. The second sample set (Sample Set Two or SST) included control and poly(DMA-co-GMA) coated poly(HEMA-co-HOHEXMA) intraocular lens implants passed through implantation inserters. The third sample set (Sample Set Three or SSR) included control and poly(DMA-co-GMA) coated poly(HEMA-co-HOHEXMA) intraocular lens implants processed through five-year stability equivalency.

Sample intraocular lenses from the three separate sample sets described above were analyzed by x-ray photoelectron spectroscopy (XPS) and time of flight-secondary mass spectrometry (ToF-SIMS) to determine the extent of the applied coating, the durability of the coating and the stability of the coating. Results of each are discussed below.

A. Sample Set One:

Sample intraocular lens implants from SSO underwent XPS analysis to determine the extent of surface modification. The results of the XPS analysis of SSO are set forth below in Table 4. Compared to controls, the coated lens implants contained an unique elemental tag, nitrogen. The nitrogen content of the control lens implants statistically increased when coated from 1.0 to 5.0 percent indicating the poly(DMA-co-GMA) coating had been applied. The 1.0 percent nitrogen on the control lens is usually biological contamination. The level of nitrogen, 5.0 percent, on the coated lens implants is indicative of a 35-angstrom thick coating. To eliminate the possibility that the 5.0 percent nitrogen on the coated lens implants was biological contamination, ToF-SIMS analysis was performed.

TABLE 4

XPS Results for SSO

|  |  | [C] | [O] | [N] | [Si] |
|---|---|---|---|---|---|
| Control |  |  |  |  |  |
| Ant. | Mean | 74.9 | 24.7 | 0.4 | 0.1 |
|  | SD | 3.2 | 3.3 | 0.3 | 0.1 |
| Post | Mean | 71.6 | 27.4 | 1.0 | 0.0 |
|  | SD | 0.4 | 0.3 | 0.2 | 0.0 |
| Test |  |  |  |  |  |
| Ant. | Mean | 74.3 | 20.8 | 4.7 | 0.2 |
|  | SD | 2.3 | 3.0 | 0.4 | 0.3 |
| Post | Mean | 73.0 | 21.1 | 5.6 | 0.3 |
|  | SD | 2.1 | 1.2 | 1.0 | 0.3 |

Figure 2:
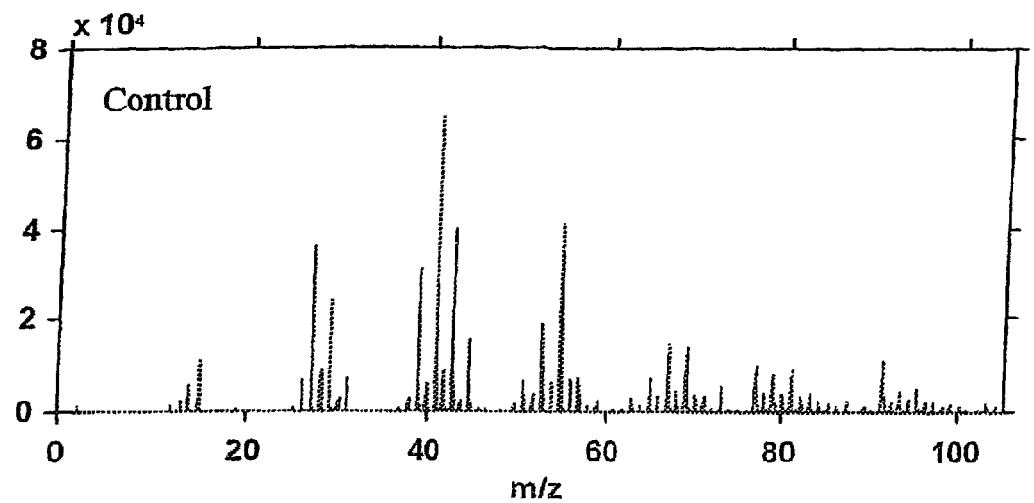
FIG. 2 shows the ToF-SIMS spectrum of control lens Implants of sample set one.

ToF-SIMS analysis was conducted on SSO to determine the presence of poly(DMA-co-GMA) polymer on the coated samples. ToF-SIMS produces a mass spectra which provides an unique "fingerprint" spectra of the polymers present at the surface. The poly-DMA fingerprint contains m/z peaks at 44D, 58D, 72D, 84D, 98D and 100D. These peaks correspond to positively charged chemical species $C_2H_6N+$, $C_3H_8N+$, $C_3H_6NO+$, $C_5H_{10}N+$, $C_5H_8NO+$ and $C_5H_{10}NO+$, respectively. All of these peaks were present on the coated sample. See FIG. 1 below. Peaks 98D and 100D were also detected in the control spectra. See FIG. 2 below. These two peaks can occur from biological contamination. However, only the detection of all of the peaks indicates the presence of the poly(DMA-co-GMA) polymer.

B. Sample Set Two:

Samples from SST having been passed through one of two differing implantation inserters (Inserter 1 and Inserter 2) underwent XPS analysis to determine the durability of the poly(DMA-co-GMA) coating by measuring the remaining levels of polymer coating on the surface thereof. The results of the XPS analysis of SST are set forth below in Table 5. Compared to the control lens implants, the coated lens implants contained an unique elemental tag, nitrogen. The nitrogen content of the control lens implants was approximately 1.0 percent or less as compared to that of the coated lens implants, which had nitrogen levels of 3.4 to 4.4 percent. The higher level of nitrogen detected on the coated lens implants indicated that the poly(DMA-co-GMA) coating was present on the lens implants after having been passed through an implantation inserter. The 1.0 percent nitrogen on the control lens implants is usually biological contamination. Compared to coated lens implants of SSO, the nitrogen content was reduced in the coated lens implants of SST, i.e., from 5.0 percent to 3.4 to 4.4 percent. The reduction in nitrogen content in SST coated lens implants indicates that some of the coating was removed, approximately 10 to 30 percent, during passage of the lens implants through the implantation inserters. To eliminate the possibility that the 3.4 to 4.4 percent nitrogen on the coated lens implants was biological contamination, ToF-SIMS was performed.

TABLE 5

XPS Results for SST

|  |  | [C] | [O] | [N] |
|---|---|---|---|---|
| Control - Inserter 1 |  |  |  |  |
| Ant. | Mean | 72.4 | 26.7 | 1.0 |
|  | SD | 1.8 | 1.7 | 0.1 |
| Post | Mean | 76.7 | 22.5 | 0.8 |
|  | SD | 1.6 | 1.7 | 0.1 |
| Test - Inserter 1 |  |  |  |  |
| Ant. | Mean | 73.2 | 23.4 | 3.4 |
|  | SD | 2.4 | 1.8 | 0.6 |
| Post | Mean | 72.8 | 22.8 | 4.4 |
|  | SD | 3.9 | 3.0 | 0.9 |
| Control - Inserter 2 |  |  |  |  |
| Ant. | Mean | 72.0 | 27.6 | 0.4 |
|  | SD | 0.6 | 0.8 | 0.4 |
| Post | Mean | 74.5 | 24.8 | 0.7 |
|  | SD | 2.9 | 2.9 | 0.1 |
| Test - Inserter 2 |  |  |  |  |
| Ant. | Mean | 75.2 | 20.7 | 4.1 |
|  | SD | 4.8 | 4.2 | 0.6 |
| Post | Mean | 76.9 | 19.4 | 3.7 |
|  | SD | 2.4 | 2.2 | 0.3 |

Figure 3:
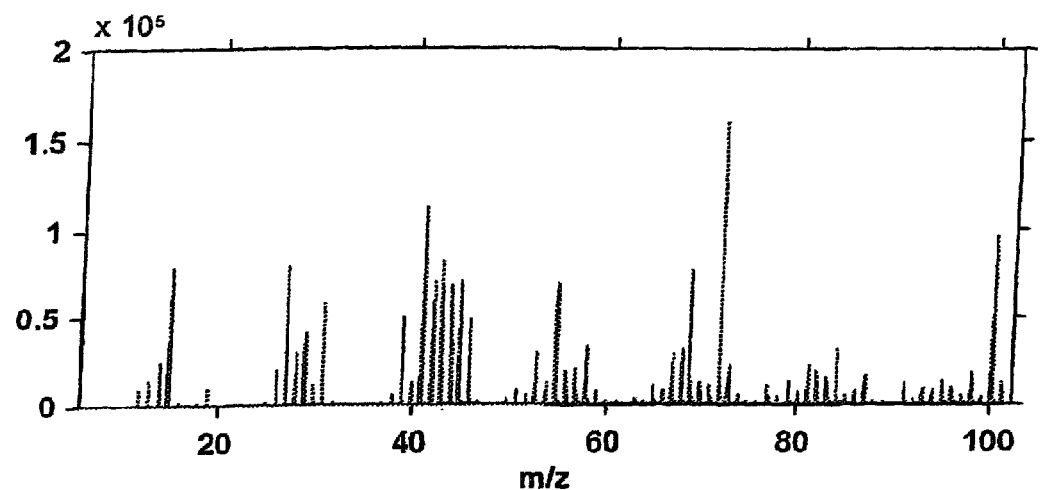
FIG. 3 shows the ToF-SIMS spectrum of poly(DMA-co-GMA) coated lens implants of sample set two passed through inserter 1.
Figure 4:
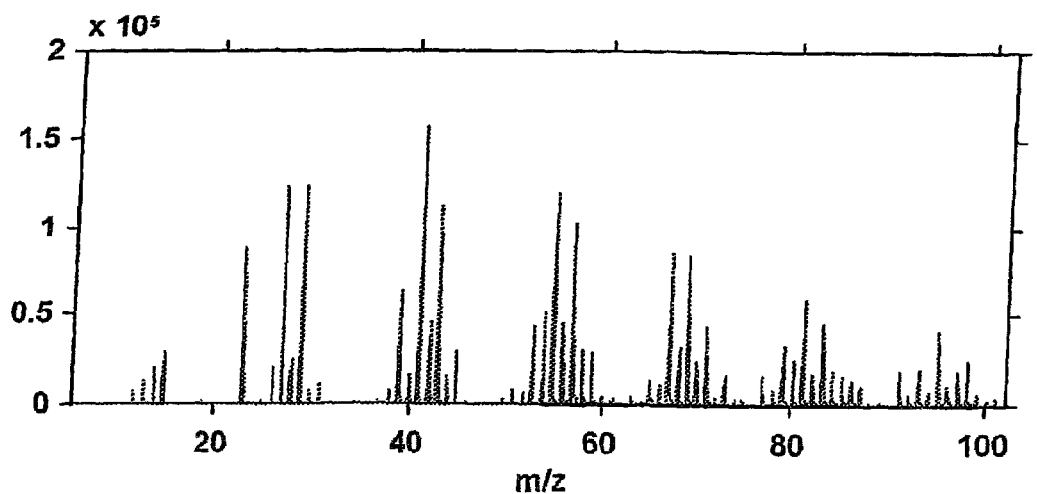
FIG. 4 shows the ToF-SIMS spectrum of posterior control lens implants of sample set two passed through inserter 1.

ToF-SIMS analysis was conducted on SST to determine the presence of poly(DMA-co-GMA) polymer on the coated samples. ToF-SIMS produces a mass spectra which provides an unique "fingerprint" spectra of the polymers present at the surface. The poly-DMA fingerprint contains m/z peaks at 44D, 58D, 72D, 84D, 98D and 100D. These peaks correspond to positively charged chemical species $C_2H_6N+$, $C_3H_8N+$, $C_3H_6NO+$, $C_5H_{10}N+$, $C_5H_8NO+$ and $C_5H_{10}NO+$, respectively. All of these peaks were present on the coated samples passed through an implantation inserter. See FIG. 3 below. The TOF-SIMS results illustrated in FIG. 3 below are of the anterior Inserter 1 coated samples. The anterior Inserter 1 coated samples were identified as the samples having undergone the most stress. Peaks 98D and 100D were also detected in the control spectra. See FIG. 4 below. These two peaks can occur from biological contamination. However, only the detection of all of the peaks indicates the presence of the poly(DMA-co-GMA) polymer.

C. Sample Set Three:

Sample intraocular lens implants from SSR were tested for a simulated interval of five years to determine the stability of the poly(DMA-co-GMA) coating. Control and coated lens implants underwent XPS analysis to determine the remaining levels of poly(DMA-co-GMA) polymer coating at the surface thereof. The results of the XPS analysis of SSO are set forth below in Table 6. Compared to controls, the coated lens implants contained an unique elemental tag, nitrogen. The nitrogen content of the control lens implants was approximately 0.9 percent. The nitrogen content of the coated lens implants was approximately 3.8 percent, indicating that the poly(DMA-co-GMA) coating was present following stability testing. The 0.9 percent nitrogen on the control lens is usually biological contamination. Compared to coated lens implants of SSO, the nitrogen content was reduced in the coated lens implants of SSR, i.e., from 5.0 percent to 3.8 percent. The reduction in nitrogen content in SSR coated lens implants indicates that some of the coating was lost, approximately 24 percent, after five simulated years. To eliminate the possibility that the 3.8 percent nitrogen on the coated lens implants was biological contamination, ToF-SIMS analysis was performed.

TABLE 6

XPS Results for SSR

|  |  | [C] | [O] | [N] | [Si] |
|---|---|---|---|---|---|
| Control |  |  |  |  |  |
| Ant. | Mean | 77.7 | 21.3 | 0.9 | 0.0 |
|  | SD | 1.0 | 1.4 | 0.4 | 0.0 |
| Post | Mean | 75.1 | 24.0 | 0.9 | 0.0 |
|  | SD | 0.4 | 0.5 | 0.2 | 0.0 |
| Test |  |  |  |  |  |
| Ant. | Mean | 75.7 | 20.0 | 3.8 | 0.5 |
|  | SD | 2.0 | 1.0 | 0.3 | 0.9 |
| Post | Mean | 78.5 | 17.3 | 3.7 | 0.5 |
|  | SD | 0.6 | 1.1 | 0.2 | 0.2 |

Figure 5:
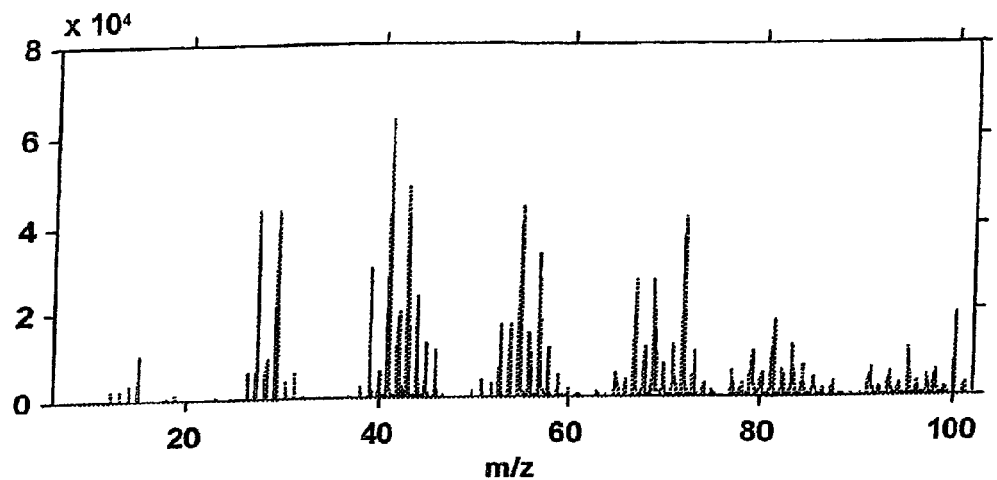
FIG. 5 shows the ToF-SIMS spectrum of anterior poly(DMA-co-GMA) coated lens implants of sample set three.
Figure 6:
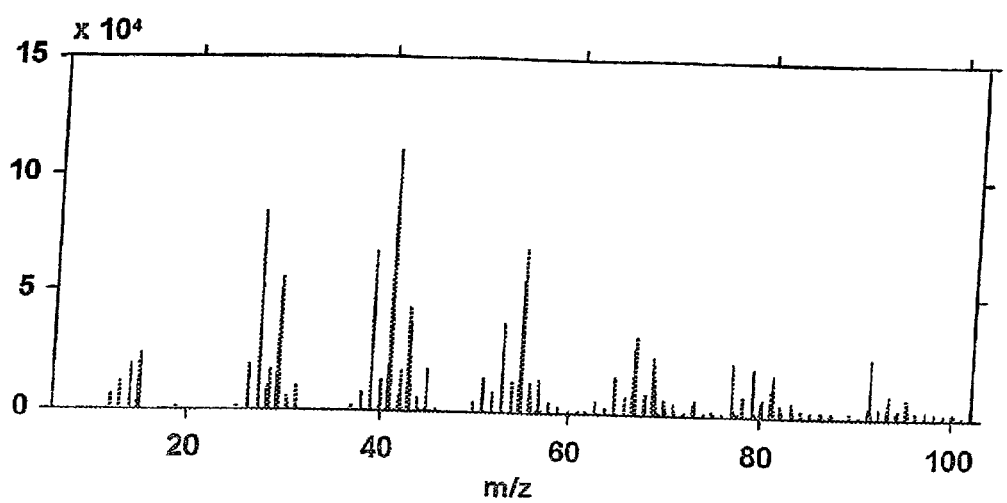
FIG. 6 shows the ToF-SIMS spectrum of posterior control lens implants of sample set three.

ToF-SIMS analysis was conducted on SSR to determine the presence of poly(DMA-co-GMA) polymer on the coated samples. ToF-SIMS produces a mass spectra which provides an unique "fingerprint" spectra of the polymers present at the surface. The poly-DMA fingerprint contains m/z peaks at 44D, 58D, 72D, 84D, 98D and 100D. These peaks correspond to positively charged chemical species $C_2H_6N+$, $C_3H_8N+$, $C_3H_6NO+$, $C_5H_{10}N+$, $C_5H_8NO+$ and $C_5H_{10}NO+$, respectively. All of these peaks were present on the coated sample. See FIG. 5 below. Peaks 98D and 100D were also detected in the control spectra. See FIG. 6 below. These two peaks can occur from biological contamination. However, only the detection of all of the peaks indicates the presence of the poly(DMA-co-GMA) polymer.

EXAMPLE 20

Surface Modification of Poly(HEMA-co-HO-HEXMA) Intraocular Lens Implant with Reactive, Hydrophilic Copolymer of N,N-dimethylacrylamide (DMA), 1H,1H,5H-octafluoropentylmethacrylate (OFPMA) and Glycidyl Methacrylate (GMA) from Example 6

Poly (HEMA-co-HOHEXMA) intraocular lens implants were surface modified or coated by placing the intraocular lens implants in a container and adding a 1.0 percent by weight poly (DMA-co-OFPMA-co-GMA [84/1.5/14.5 mole %]) solution to the container to cover the intraocular lens implants. The container containing the intraocular lens implants covered in solution was then autoclaved for 59 minutes at 121° Celsius. The container was then removed from the autoclave and the intraocular lens implants were removed from the solution. The intraocular lens implants were then rinsed three times in a buffered saline solution.

EXAMPLE 21

Bovine Lens Epithelial Cell Attachment and Growth Test

Bovine lens epithelial cells (LECs) were cultured on a range of test materials the results of which are set forth below in Table 7.

TABLE 7

Percent Confluence of Bovine LECs on Biomaterials

|  | Day 1 | Day 3 | Day 7 | Day 14 | Day 21 | Day 28 | Day 35 | Day 42 |
|---|---|---|---|---|---|---|---|---|
| Coated Material* | 0% | 0% | 0% | 0% | 0% | 0% | 0% | 0% |
| Coated Material* | 0% | 0% | 0% | 0% | 0% | 0% | 0% | 0% |
| Hydrogel (18% $H_2O$) | 25% | 30% | 90% | 100% | 100% | 100% | 99% | 99% |
| PMMA | 25% | 30% | 70% | 90% | 95% | 100% | 75% | 75% |
| Control** | 70% | 100% | 100% | 100% | 100% | 100% | 100% | 95% |

Seeding density = 56,000 cells

*Copolymer from Example 6 (DMA-OFPMA-GMA)

**Tissue culture plastic

EXAMPLE 22

Surface Treatment of Balafilcon A Contact Lenses (PureVision® Lenses, Commercially Available from Bausch & Lomb. Inc., Rochester, N.Y.)

Balafilcon A is a silicone-hydrogel lens material containing acid functional groups. The surface treatment employed the hydrophilic reactive polymers made from Example 1 above, according to the following reaction scheme:

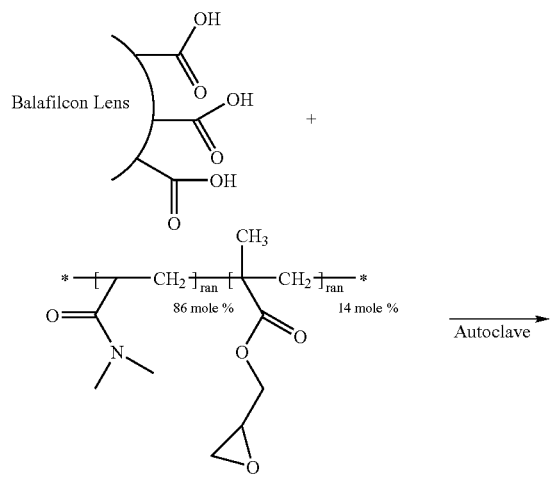

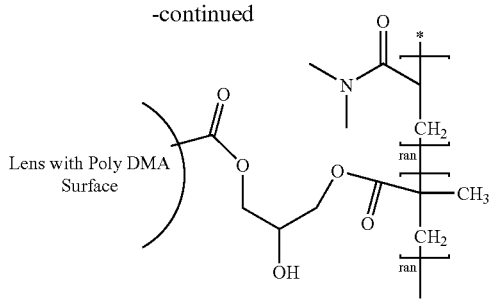

A solution of reactive polymer of Example 1 (10.0 g per 1000 ml of water) was prepared. Lenses were extracted with three changes of 2-propanol over a four-hour period and then with three changes of water at one-hour intervals. Lenses (36 samples) were then placed in the solution of reactive polymer. One drop of methyldiethanolamine was added to catalyze the reaction. The lenses were put through one 30-minute autoclave cycle.

EXAMPLE 23

Surface Treatment of Balafilcon A Contact Lenses (PureVision® Lenses, Commercially Available from Bausch & Lomb. Inc., Rochester, N.Y.)

The surface treatment employed the hydrophilic reactive polymers made from Example 6 above, according to the following reaction scheme:

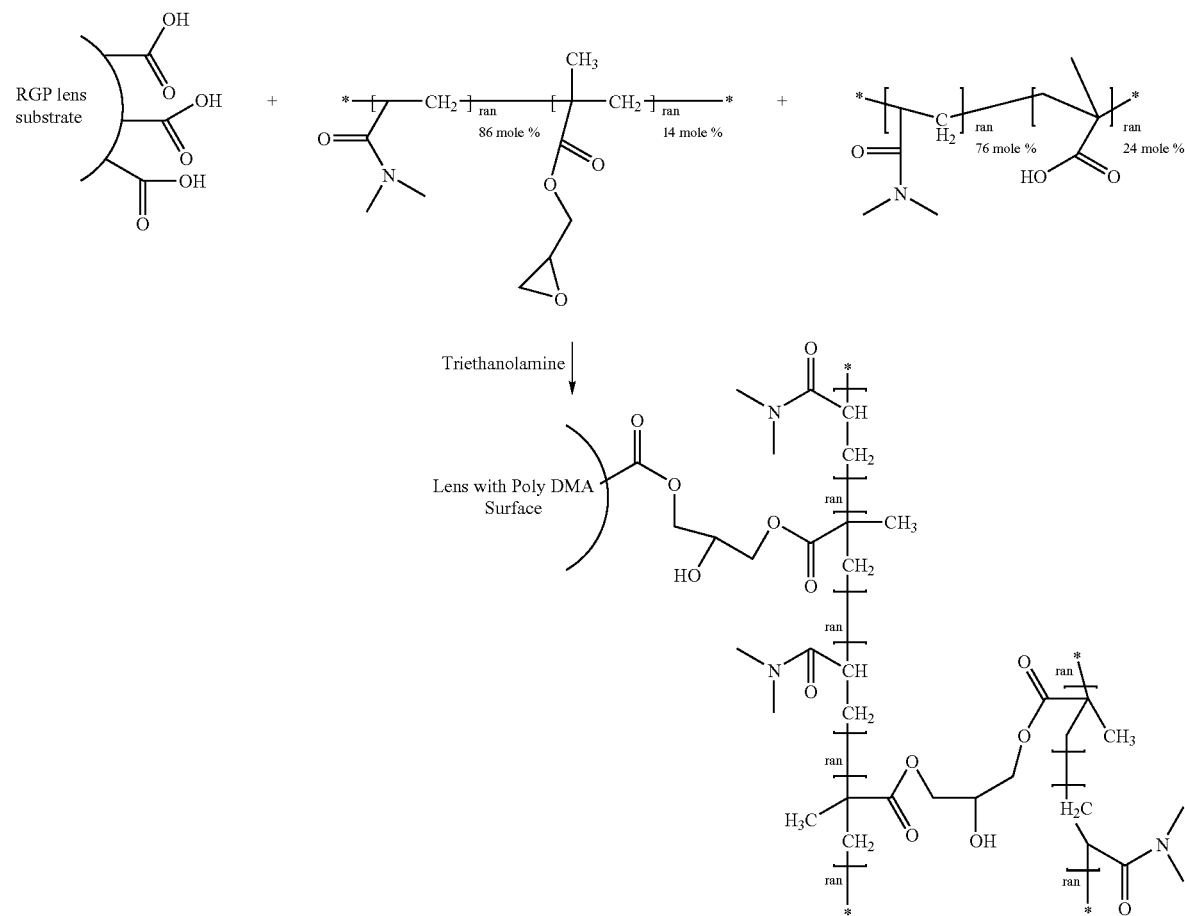

Two solutions of reactive polymer of Example 6 were prepared (See Table 8 below). Lenses were extracted in 2-propanol for 4 hours and then placed in purified water for 10 minutes. The water bath was then changed and lenses were allowed to soak for an additional 10 minutes. Lenses (30 samples) were then placed in each solution of reactive polymer with one drop of methyldiethanolamine to catalyze the reaction. The lenses were put through one 30-minute autoclave cycle. The solution in the vials was then replaced with purified water two times and the lens samples were again autoclaved. This procedure was used to remove, any hydrophilic polymer not chemically bonded to the lens samples.

TABLE 8

| Sample | Polymer Concentration | # of Lenses treated |
|---|---|---|
| A | 1.0% (2.5 g/250 ml $H_2O$) | 30 |
| B | 2.0% (5 g/250 ml $H_2O$) | 30 |
| Control | None | 30 |

Figure 7:
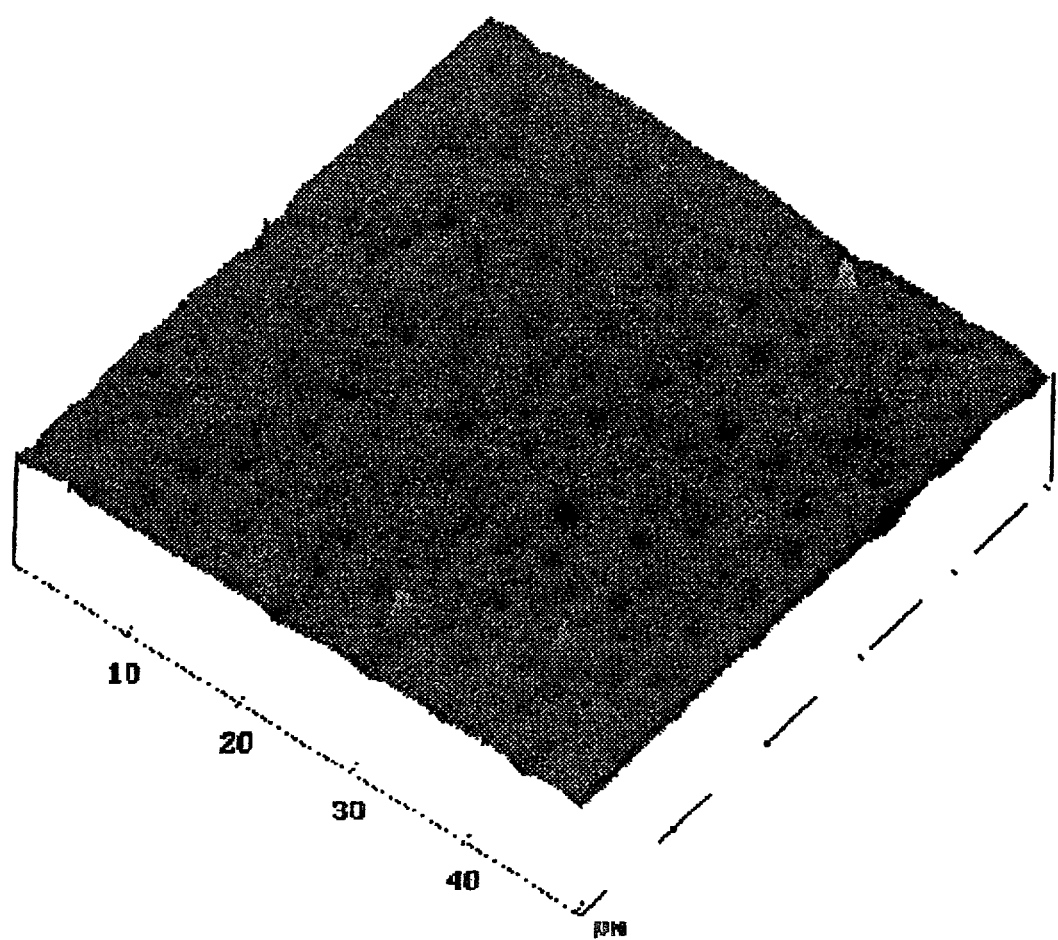
FIG. 7 shows AFM image of a Purevision® lens with no surface treatment.
Figure 8:
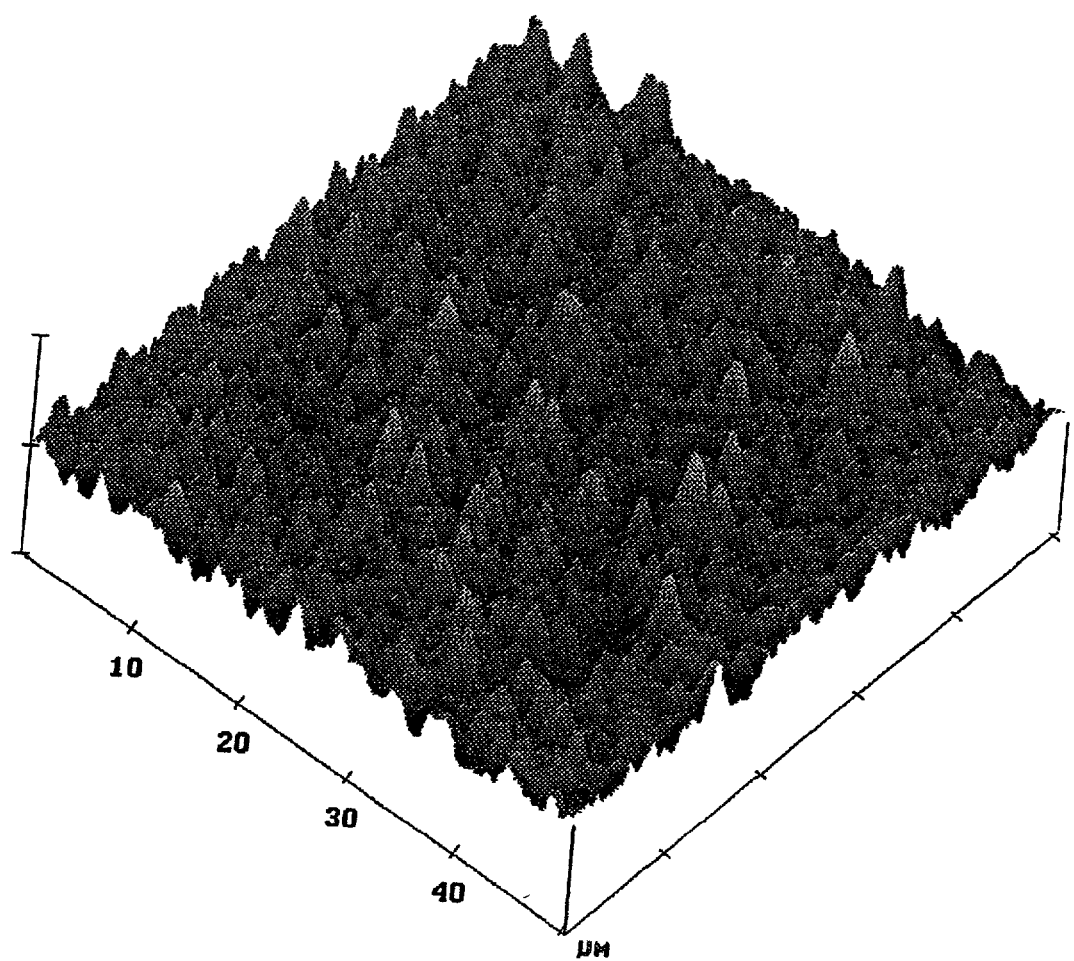
FIG. 8 shows AFM image of a polymer coated Purevision® lens of Example 23, sample A.
Figure 9:
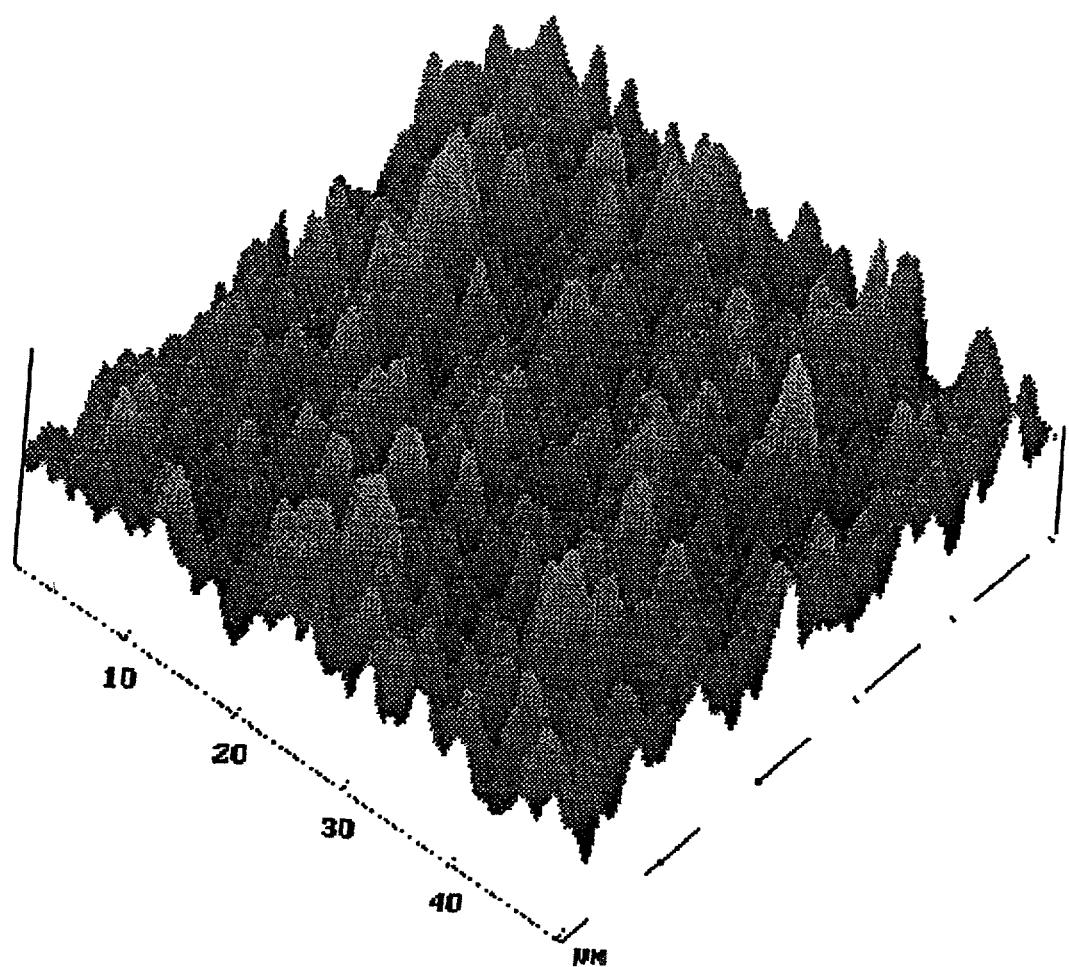
FIG. 9 shows AFM image of a polymer coated Purevision® lens of Example 23, sample B.

The atomic force microscopy (AFM) images of the control (FIG. 7 below) when compared to samples A (FIG. 8 below) and B (FIG. 9 below) clearly show that the hydrophilic coating has been applied. Elemental analysis by XPS also indicates that the material surface has been modified. A Physical Electronics [PHI] Model 5600 XPS was used for the surface characterization. This instrument utilized a monochromated Al anode operated a 300 watts, 15 kV and 20 milliamps. The base pressure of the instrument was $2.0 \times 10^{-10}$ torr and during operation the pressure was $5.0 \times 10^{-8}$ torr. This instrument made use of a hemispherical analyzer. The instrument had an Apollo workstation with PHI 8503A version 4.0A software. The practical measure for sampling depth for this instrument at a sampling angle of 45° was 74 Å.

Each specimen was analyzed utilizing a low-resolution survey spectra (0–1100 eV) to identify the elements present on the sample surface (10–100 Å). Surface elemental compositions were determined from high-resolution spectra obtained on the elements detected in the low-resolution survey scans. Those elements included oxygen, nitrogen, carbon, silicon and fluorine. Quantification of elemental compositions was completed by integration of the photoelectron peak areas after sensitizing those areas with the instrumental transmission function and atomic cross sections for the orbitals of interest. The XPS data is given in Table 9 below.

TABLE 9

| Sample | | O1s | N1s | C1s | Si2p | F1s |
|---|---|---|---|---|---|---|
| Control Posterior | Average | 17.7 | 7.2 | 66.9 | 8.1 | 0.0 |
| | std dev | 0.9 | 0.2 | 0.8 | 0.3 | 0.0 |
| Control Anterior | Average | 17.9 | 7.0 | 66.9 | 8.2 | 0.0 |
| | std dev | 0.6 | 0.6 | 0.7 | 0.4 | 0.0 |
| A Posterior | Average | 17.9 | 8.9 | 69.5 | 1.8 | 2.0 |
| | std dev | 0.3 | 0.2 | 0.6 | 0.6 | 0.2 |
| A Anterior | Average | 17.7 | 9.1 | 69.7 | 1.7 | 1.9 |
| | std dev | 0.3 | 0.3 | 0.8 | 0.3 | 0.2 |
| B Posterior | Average | 18.0 | 8.9 | 69.9 | 1.2 | 2.1 |
| | std dev | 0.3 | 0.5 | 1.0 | 0.1 | 0.4 |
| B Anterior | Average | 17.8 | 8.8 | 70.0 | 1.3 | 2.0 |
| | std dev | 0.2 | 0.3 | 0.6 | 0.3 | 0.0 |
| Theoretical Atomic Conc. DMA-co-OFPMA-co-GMA From Example 11 | | 17.1 | 11.0 | 70.1 | 0.0 | 1.8 |

EXAMPLE 24

Surface Treatment of a Rigid Gas Permeable (RGP) Lens

A Quantum® II RGP lens, commercially available from Bausch & Lomb, Inc., manufactured from a fluorosilicone acrylate material containing acid groups, was surface treated according to the following reaction scheme.

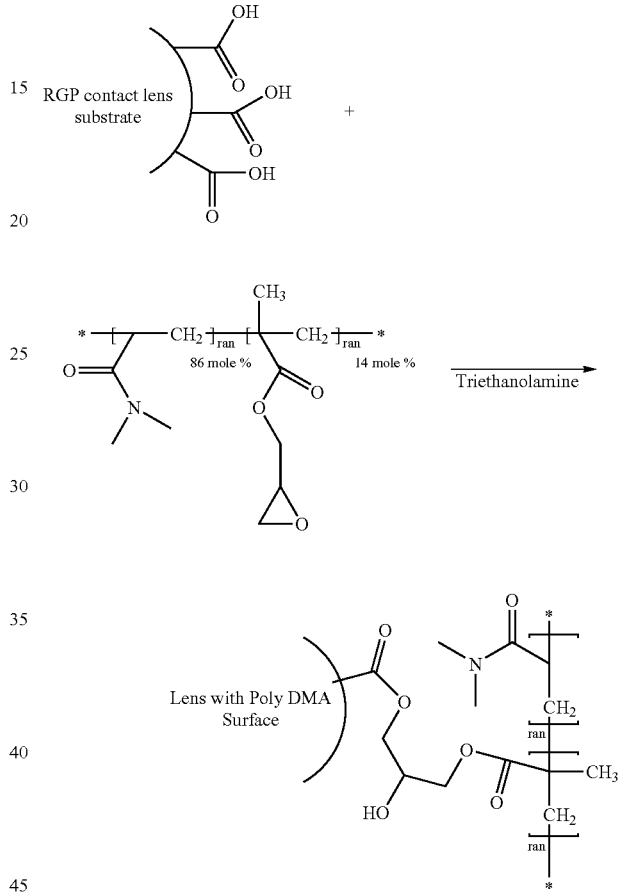

A solution of reactive polymer of Example 1 (5.0 g per 100 ml of water) was prepared. Lenses (20 samples) were then placed in the solution of reactive polymer with two (2) drops of triethanolamine and heated to 55° C. for one (1) hour. The surface-coated lenses were then rinsed off twice with purified water and allowed to dry. A drop of water placed on an untreated lens would bead up and roll off the surface while a drop of water was placed on the treated lens spread completely, wetting the lens surface.

X-ray Photo Electron Spectroscopy (XPS) data was obtained. A Physical Electronics [PHI] Model 5600 XPS was used for the surface characterization. This instrument utilized a monochromated Al anode operated a 300 watts, 15 kV and 20 milliamps. The base pressure of the instrument was $2.0 \times 10^{-10}$ torr and during operation the pressure was $5.0 \times 10^{-8}$ torr. This instrument made use of a hemispherical analyzer. The instrument had an Apollo workstation with PHI 8503A version 4.0A software. The practical measure for sampling depth for this instrument at a sampling angle of 45° was 74 Å.

Each specimen was analyzed utilizing a low-resolution survey spectra (0–1100 eV) to identify the elements present on the sample surface (10–100 Å). Surface elemental compositions were determined from high-resolution spectra obtained on the elements detected in the low-resolution survey scans. Those elements included oxygen, nitrogen, carbon, silicon and fluorine. Quantification of elemental compositions was completed by integration of the photoelectron peak areas after sensitizing those areas with the instrumental transmission function and atomic cross sections for the orbitals of interest. The XPS data for the coated lenses and controls are given in Table 10 below.

TABLE 10

| Lot ID | | O | N | C | Si | F |
|---|---|---|---|---|---|---|
| Lens Posterior | Average | 22.3 | 4.8 | 54.4 | 10.3 | 10.9 |
|  | Std dev |  |  |  |  |  |
| Lens Anterior | Average | 19.1 | 6.7 | 63.4 | 2.7 | 8.1 |
|  | std dev | 0.6 | 0.3 | 1.1 | 0.6 | 0.7 |
| Quantum ® II Control | Average | 18.7 | 0.0 | 56.1 | 5.2 | 20.0 |
| (post & ant are the same) | std dev | 0.5 | 0.0 | 0.7 | 0.3 | 0.4 |

TABLE 10-continued

| Lot ID | O | N | C | Si | F |
|---|---|---|---|---|---|
| Theoretical Atomic Concentrations for DMA-co-GMA Reactive Polymer | 17 | 12 | 71 | 0 | 0 |

EXAMPLE 25

Surface Treatment of a Rigid Gas Permeable (RGP) Lens

Surface treatment of an Quantum® II RGP lens, commercially available from Bausch & Lomb, Inc., was performed according to the following reaction sequence. A two polymer coating system having complementary reactive functional groups was employed in this example. The two polymers of the coating system react with each other to form cross-linkages and also react with the lens surface.

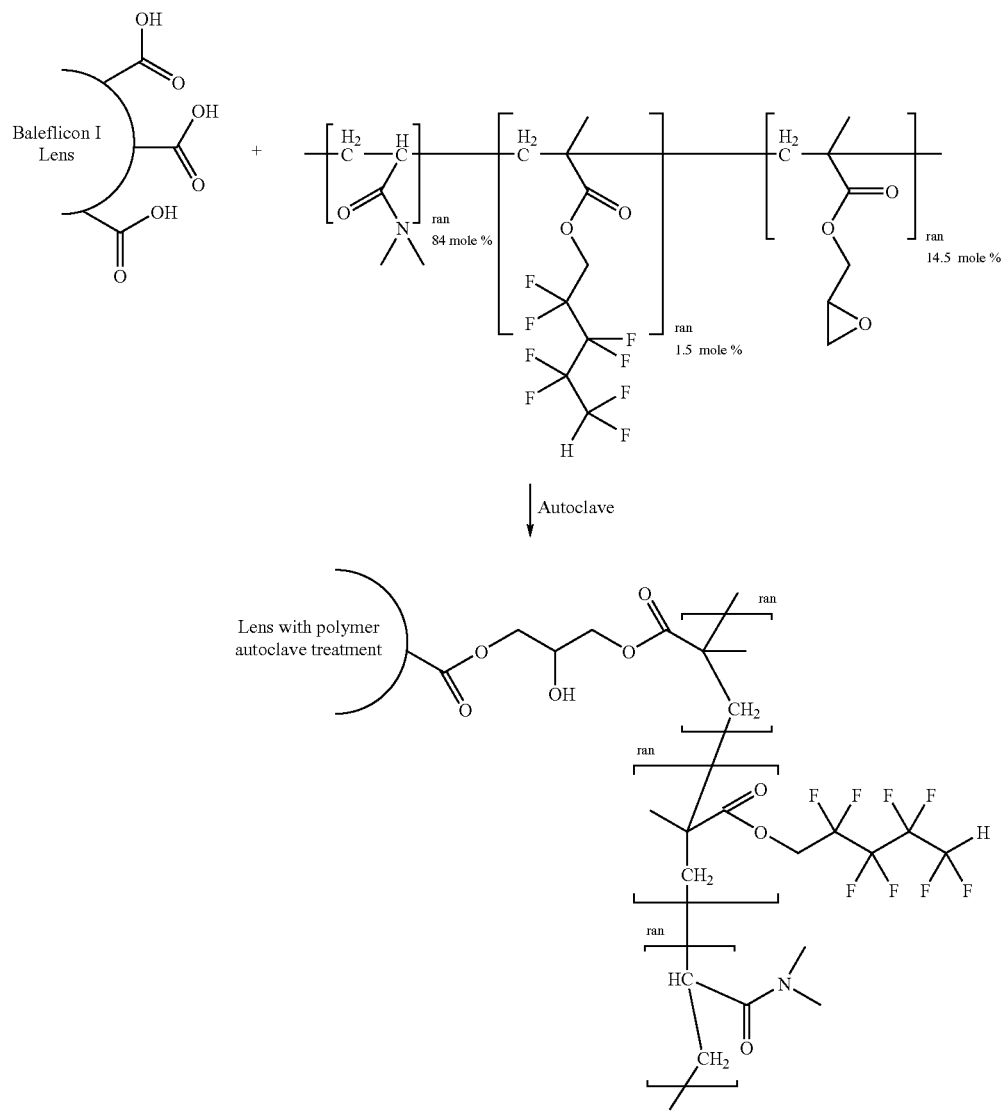

Figure 10:
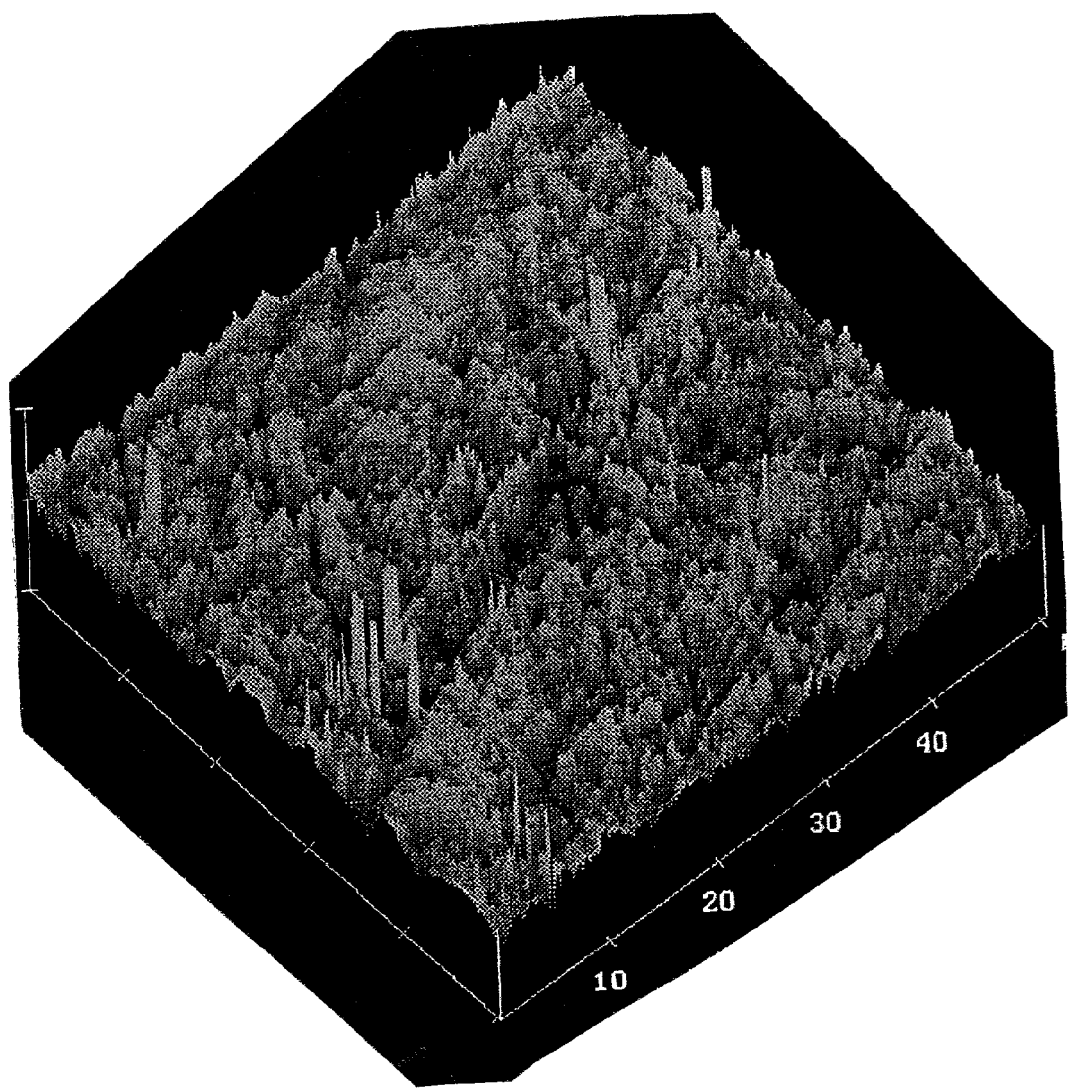
FIG. 10 shows AFM image of Quantum® II lens surface without coating.
Figure 11:
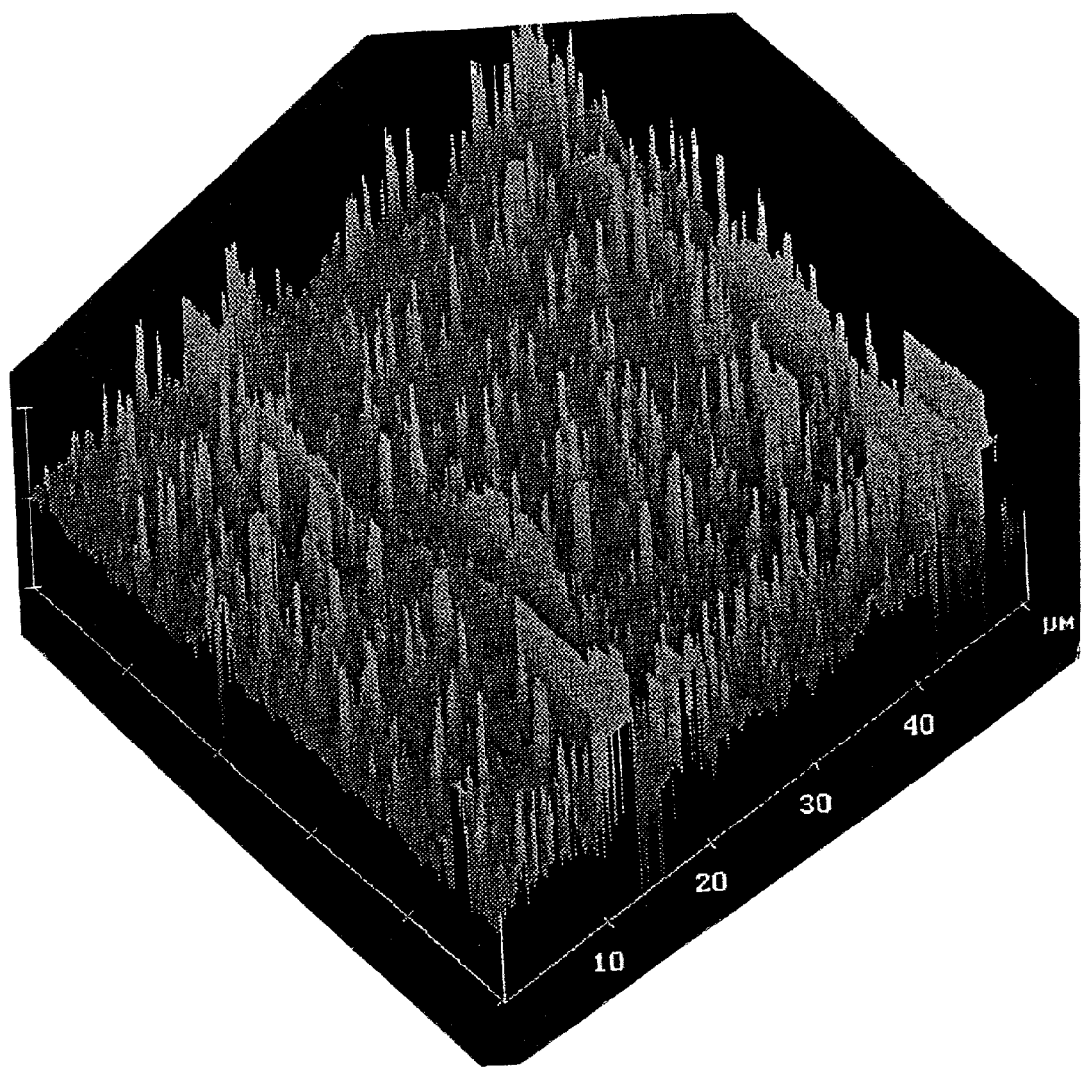
FIG. 11 shows AFM image of a polymer coated Quantum® II lens surface of Example 24.
Figure 12:
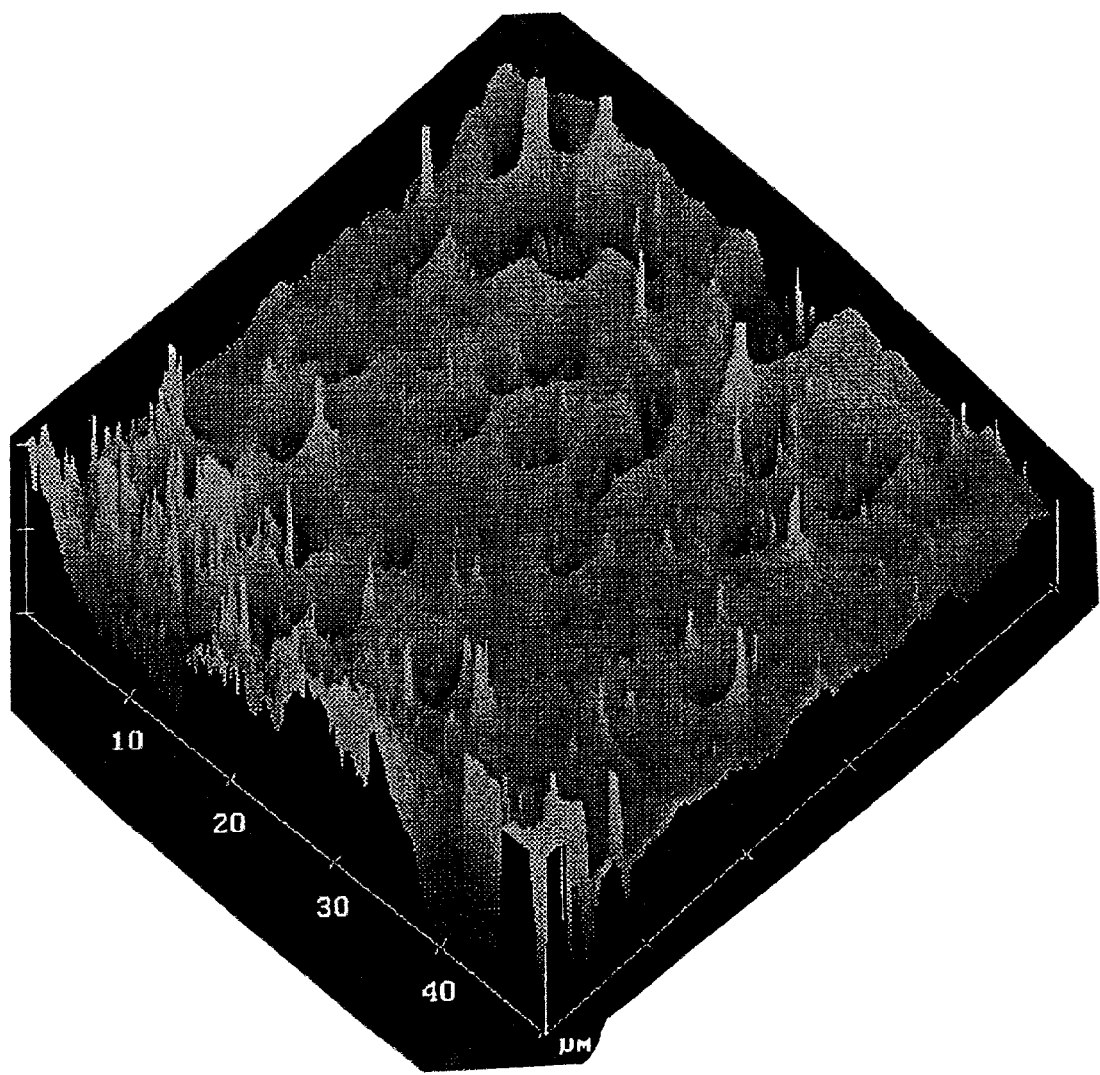
FIG. 12 shows AFM image of a polymer coated Quantum® II lens surface of Example 25.

A solution of reactive polymers of Example 1 and Example 14 above (2.5 g of each polymer per 100 ml of water) was prepared. The mixture of polymers was used in an attempt to build a thicker polymer coating via a layering effect. Lenses (20 samples) were then placed in the solution of reactive polymer with two drops of triethanolamine and heated to 55° C. for one hour. The surface-coated lenses were then rinsed off twice with purified water and allowed to dry. A drop of water placed on an untreated lens would bead up and roll off the surface while a drop of water placed on the treated lens spread completely wetting the lens surface. Atomic Force Microscopy (AFM) analysis suggests that the combination of polymers gave a thicker polymer coating. Comparisons between a Quantum® II lens with no polymer coating, the polymer coating of Example 24 and the subject coating (Example 25) are shown in FIGS. 10–12 respectively.

X-ray Photo Electron Spectroscopy (XPS) data was obtained at the Surface Science lab within Bausch and Lomb. A Physical Electronics [PHI] Model 5600 XPS was used for the surface characterization. This instrument utilized a monochromated Al anode operated a 300 watts, 15 kV and 20 milliamps. The base pressure of the instrument was $2.0 \times 10^{-10}$ torr and during operation the pressure was $5.0 \times 10^{-8}$ torr. This instrument made use of a hemispherical analyzer. The instrument had an Apollo workstation with PHI 8503A version 4.0A software. The practical measure for sampling depth for this instrument at a sampling angle of 45° was 74 Å.

Each specimen was analyzed utilizing a low-resolution survey spectra (0–1100 eV) to identify the elements present on the sample surface (10–100 Å). Surface elemental compositions were determined from high-resolution spectra obtained on the elements detected in the low-resolution survey scans. Those elements included oxygen, nitrogen, carbon, silicon and fluorine. Quantification of elemental compositions was completed by integration of the photoelectron peak areas after sensitizing those areas with the instrumental transmission function and atomic cross sections for the orbitals of interest. The XPS data for the coated lenses and controls are given in Table 11 below.

TABLE 11

| Lot ID | | O | N | C | Si | F |
| --- | --- | --- | --- | --- | --- | --- |
| Lens Posterior | Average | 18.8 | 8.0 | 67.6 | 3.7 | 2.6 |
|  | std dev |  |  |  |  |  |
| Lens Anterior | Average | 18.4 | 4.2 | 62.8 | 4.1 | 10.5 |
|  | std dev | 0.5 | 1.2 | 1.7 | 0.4 | 3.1 |
| Quantum ® II Control | Average | 18.7 | 0.0 | 56.1 | 5.2 | 20.0 |
| (post & ant are the same) | std dev | 0.5 | 0.0 | 0.7 | 0.3 | 0.4 |
| Theoretical Atomic Concentrations for DMA-co-GMA Reactive Polymer |  | 17 | 12 | 71 | 0 | 0 |

EXAMPLE 26

Surface Modification of 3-Phenylpropyl Acrylate and N,N-dimethylacrylamide Cast Film A film was cast using 75 parts of 3-phenylpropyl acrylate, 25 parts of N,N-dimethylacrylamide, 2 parts of ethylene glycol dimethacrylate, 5 parts of glycidyl methacrylate and 0.5 percent by weight Irgacure™ 819 (Ciba-Geigy, Basel, Switzerland) as the photoinitiator. The cure conditions consisted of two hours of ultraviolet irradiation. The films are hydrated in a solution that contains 1 percent by weight of polyacrylic acid and 0.5 percent by weight of a 80/20 copolymer of N,N-dimethylacrylamide and glycidyl methacrylate. The film is autoclaved for thirty minutes. The resultant film is wettable and lubricious demonstrating that the polymer coating is applied.

EXAMPLE 27

Surface Modification of 3-Phenylpropyl Acrylate and N,N-dimethylacrylamide Cast Film A film was cast using 75 parts of 3-phenylpropyl acrylate, 25 parts of N,N-dimethylacrylamide, 2 parts of ethylene glycol dimethacrylate, 5 parts of methacrylic acid and 0.5 percent by weight Irgacure™ 819 as the photoinitiator. The cure conditions consisted of two hours of ultraviolet irradiation. The films are hydrated in a solution that contains 1 percent by weight of a 80/20 copolymer of N,N-dimethylacrylamide and glycidyl methacrylate. The films are autoclaved for thirty minutes. The resultant films are wettable and lubricious demonstrating that the polymer coating is applied.

EXAMPLE 28

Surface Modification of Polydimethylsiloxane Octafluoropentyl Methacrylate and 2-vinyl-4,4-dimethyl-2-oxazolin-5-one Cast Film A film was cast using 80 parts of DP 100 methacrylate end-capped polydimethylsiloxane containing 65 mole percent of a trifluoropropyl side chain, 20 parts of octafluoropentyl methacrylate, 5 parts of 2-vinyl-4,4-dimethyl-2-oxazolin-5-one and 0.5 percent by weight Irgacure™ 819 as the photoinitiator. The cure conditions consisted of two hours of ultraviolet irradiation. The films are hydrated in a solution that contained 1 percent by weight of a 80/20 copolymer of N,N-dimethylacrylamide and glycidyl methacrylate. The films are autoclaved for thirty minutes. The resultant films are wettable and lubricious demonstrating that the polymer coating is applied.

Surface modified IOLs manufactured in accordance with the present invention can be of any design capable of being rolled or folded into a small cross section that can fit through a relatively small incision, i.e., 4.0 mm or less. For example, IOLs can be of a one-piece or multipiece design, and comprise optic and haptic portions. The optic portion is that portion which serves as the lens and the haptic portions are attached to the optic portion to hold the optic portion in proper alignment within an eye. The haptic portions may be integrally formed with the optic portion in a one-piece design or attached by staking, adhesives or other methods known to those skilled in the art in a multipiece design.

The subject IOLs may be manufactured to have the optic portion and the haptic portions made of the same or different materials. Preferably, in accordance with the present invention, the optic portion and the haptic portions are made of the same high-refractive index, low glass transition temperature composition. However, the optic portion and the haptic portions may also be manufactured from different compositions-and/or different formulations of the same composition as described in detail in U.S. Pat. Nos. 5,217,491 and 5,326,506, each incorporated herein in their entirety by reference. Once the particular composition is selected, the material is either cast in molds of the desired shape or cast in the form of rods and lathed into disks. These disks are then machined at low temperatures below the glass transition temperature into IOLs. The IOLs whether molded or machined are then cleaned, polished, packaged and sterilized by customary methods known to those skilled in the art.

In addition to IOLs, the methods and materials of the present invention are also suitable for use with other ophthalmic devices such as contact lenses, keratoprostheses, capsular bag extension rings, corneal inlays, corneal rings or like devices.

IOLs manufactured using the unique materials of the present invention are used as customary in the field of ophthalmology. In a surgical procedure, an incision is placed in the cornea of an eye, most commonly the natural lens of the eye is removed and the IOL manufactured and coated using materials of the present invention is inserted into the posterior chamber or lens capsule of the eye prior to closing the incision. However, the subject surface modified IOL implants are also suitable for implantation in an anterior chamber of an eye if so desired. Preferably implantation is accomplished using an implantation inserter, although other techniques known to those skilled in the art of ophthalmology are likewise acceptable.

While there is shown and described herein certain specific structures and compositions of the present invention, it will be manifest to those skilled in the art that various modifications may be made without departing from the spirit and scope of the underlying inventive concept and that the same is not limited to particular structures herein shown and described except insofar as indicated by the scope of the appended claims.

We claim:

1. A surface modified medical device comprising:
   a medical device comprising a functional group-containing polymeric material that comprises monomeric units having functional groups; and
   a coating on a substantially entire surface of said medical device, said coating comprising one or more synthetic, reactive, hydrophilic polymers, wherein said hydrophilic polymers form direct covalent bonds with said functional groups of said functional group-containing polymeric material;
   wherein the functional group-containing polymeric material is selected from polymers comprising monomeric units selected from the group consisting of glyceryl methacrylate, 3-hydroxypropyl methacrylamide, acrylic acid, N-carboxy-β-alanine-N-vinyl ester, 2-isopropenyl-4, 4-dimethyl-2-oxazolin-5-one, 2-vinyl-4,4-dimethyl-2-oxazolin-5-one, spiro-4'-(2'-isopropenyl-2'-oxazolin-5-one)cyclohexane, spiro-4'-(2'-vinyl-2'-oxazolin-5'-one)cyclohexane, 2-(1-propenyl)-4,4-dimethyl-oxazolin-5-one, methacrylic anhydride, acrylic anhydride, maleic anhydride, glycidyl methacrylate, and combinations thereof; fluorocarbon polymers; polyesters; polyamides; polyurethanes; fluorine-containing polysiloxane elastomers; and combinations thereof.

2. A surface modified medical device comprising:
   a medical device comprising a functional group-containing polymeric material that comprises monomeric units having functional groups; and
   a coating on a substantially entire surface of said medical device, said coating comprising one or more reactive, hydrophilic polymers that form direct covalent bonds with said functional groups of said functional group-containing polymers;
   wherein the functional group-containing polymeric material comprises a copolymer of 2-hydroxyethyl methacrylate (HEMA) and 6-hydroxyhexyl methacrylate (HOHEXMA).

3. The medical device of claim 1 or 2 wherein said medical device is an intraocular lens.

4. The medical device of claim 1 or 2 wherein said medical device is a contact lens or a corneal inlay.

5. The surface modified medical device of claim 1 or 2 wherein said one or more reactive, hydrophilic polymers are produced from hydrophilic monomers selected from the group consisting of aprotic types and protic types.

6. The surface modified medical device of claim 1 or 2 wherein said one or more reactive, hydrophilic polymers are produced from hydrophilic monomers selected from the group consisting of N,N-dimethylacrylamide, N,N-dimethylmethacrylamide, N-methylmethacrylamide and N-methylacrylamide.

7. The surface modified medical device of claim 1 or 2 wherein said one or more reactive, hydrophilic polymers are produced from hydrophilic monomers having reactive chemical functionality selected from the group consisting of epoxide functionality, carboxylic acid functionality, anhydride functionality, oxazolinone functionality and alcohol functionality.

8. A method of using the surface modified medical device of claim 1 or 2 comprising:
   creating an incision in an eye; and
   implanting said surface modified medical device through said incision prior to closing said incision.

9. The method of using the surface modified medical device of claim 8 wherein said medical device is an intraocular lens.

10. The method of using the surface modified medical device of claim 8 wherein said medical device is a corneal inlay.

11. The method of using the surface modified medical device of claim 8, 9 or 10 wherein a natural lens is removed from said eye prior to implanting said surface modified medical device within said eye.

12. The method of using the surface modified medical device of claim 8 or 9 wherein a natural lens is removed from said eye prior to implanting said surface modified medical device within a lens capsule of said eye.

13. The method of using the surface modified medical device of claim 8, 9 or 10 wherein a natural lens is removed from said eye prior to implanting said surface modified medical device within said eye using an implantation inserter.

14. The method of using the surface modified medical device of claim 8 or 9 wherein a natural lens is removed from said eye prior to implanting said surface modified medical device within a capsule of said eye using an implantation inserter.

15. A surface modified medical device comprising:
   a medical device comprising a functional group-containing polymeric material that comprises a copolymer of HEMA and HOHEXMA; and
   a reactive, hydrophilic polymer applied to a surface of said medical device; wherein said reactive, hydrophilic polymer comprises monomeric units of dimethylacrylamide and (DMA) glycidyl methacrylate (GMA).

16. A method of making a surface modified medical device comprising:
   producing a medical device from a functional group-containing polymeric material that comprises monomeric units having functional groups;

exposing one or more synthetic, reactive, hydrophilic polymers to a substantially entire surface of said medical device; and forming a coating comprising said hydrophilic polymers on the substantially entire surface of said medical device, wherein said hydrophilic polymers form direct covalent bonds with said functional groups of said functional group-containing polymeric material;

wherein the functional group-containing polymeric material is selected from polymers comprising monomeric units selected from the group consisting of glyceryl methacrylate, 3-hydroxypropyl methacrylamide, acrylic acid, N-carboxy-β-alanine-N-vinyl ester, 2-isopropenyl-4, 4-dimethyl-2-oxazolin-5-one, 2-vinyl-4,4-dimethyl-2-oxazolin-5-one, spiro-4'-(2'-isopropenyl-2'-oxazolin-5-one) cyclohexane, spiro-4'-(2'-vinyl-2'-oxazolin-5'-one)cyclohexane, 2-(1-propenyl)-4,4-dimethyl-oxazolin-5-one, methacrylic anhydride, acrylic anhydride, maleic anhydride, glycidyl methacrylate, and combinations thereof; fluorocarbon polymers; polyesters; polyamides; polyurethanes; fluorine-containing polysiloxane elastomers; and combinations thereof.

17. A method of making a surface modified medical device comprising:
producing a medical device from a functional group-containing polymeric material that comprises monomeric units having functional groups;
exposing one or more reactive, hydrophilic polymers to a substantially entire surface of said medical device; and
forming a coating comprising said reactive, hydrophilic polymers on the substantially entire surface of said medical device, wherein said functional groups form direct covalent bonds with said reactive polymeric material;
wherein the functional group-containing polymeric material comprises a copolymer of HEMA and HOHEXMA.

18. The method of claim 16 or 17 wherein said medical device is an intraocular lens or corneal inlay.

19. The method of claim 16 or 17 wherein said medical device is a contact lens.

20. The method of claim 16 or 17 wherein said one or more reactive, hydrophilic polymers are produced from hydrophilic monomers selected from the group consisting of aprotic types and protic types.

21. The method of claim 16 or 17 wherein said one or more reactive, hydrophilic polymers are produced from hydrophilic monomers selected from the group consisting of N,N-dimethylacrylamide, N,N-dimethylmethacrylamide, N-methylmethacrylamide and N-methylacrylamide.

22. The method of claim 16 or 17 wherein said one or more reactive, hydrophilic polymers are produced from hydrophilic monomers having reactive chemical functionality selected from the group consisting of epoxide functionality, carboxylic acid functionality, anhydride functionality, oxazolinone functionality and alcohol functionality.

23. A surface modified medical device comprising:
a medical device comprising poly(HEMA-co-HOHEXMA); and
a coating on a surface of said medical device, said coating comprising a reactive, hydrophilic polymer that has functional groups that form direct covalent bonds with said surface of said medical device; wherein said reactive, hydrophilic polymer is a copolymer of DMA, GMA, and octafluoropentyl methacrylate.

24. A method of making a surface modified medical device, said method comprising:
producing a medical device from comprising poly (HEMA-co-HOHEXMA);
exposing a reactive, hydrophilic polymer to a surface of said medical device; wherein said reactive, hydrophilic polymer is a copolymer of DMA, GMA, and octafluoropentyl methacrylate; and
forming a coating comprising said copolymer of DMA, GMA, and octafluoropentyl methacrylate, wherein said reactive, hydrophilic polymer forms direct covalent bonds with said medical device.

* * * * *